(12) United States Patent
Chung et al.

(10) Patent No.: US 9,487,596 B2
(45) Date of Patent: Nov. 8, 2016

(54) COMPOUND ISOLATED FROM QUAMOCLIT, AND COMPOSITION FOR PREVENTING OR TREATING DIABETES CONTAINING THE COMPOUND AS AN ACTIVE INGREDIENT

(75) Inventors: Bong Hyun Chung, Daejeon (KR); So Yeon Yi, Daejeon (KR); Ui Jin Lee, Daejeon (KR)

(73) Assignee: NANOBIOTECH CO., LTD., Daejeon (KR)

( * ) Notice: Subject to any disclaimer, the term of this patent is extended or adjusted under 35 U.S.C. 154(b) by 86 days.

(21) Appl. No.: 14/239,136

(22) PCT Filed: Jun. 28, 2012

(86) PCT No.: PCT/KR2012/005129
§ 371 (c)(1),
(2), (4) Date: Feb. 24, 2014

(87) PCT Pub. No.: WO2013/024968
PCT Pub. Date: Feb. 21, 2013

(65) Prior Publication Data
US 2014/0179622 A1    Jun. 26, 2014

(30) Foreign Application Priority Data

Aug. 18, 2011 (KR) .................... 10-2011-0082445
Jun. 15, 2012 (KR) .................... 10-2012-0064524

(51) Int. Cl.
| | |
|---|---|
| *C07H 15/04* | (2006.01) |
| *C08B 37/00* | (2006.01) |
| *A61K 36/39* | (2006.01) |
| *C07D 407/12* | (2006.01) |
| *C07D 407/14* | (2006.01) |
| *A23L 1/29* | (2006.01) |
| *A61K 31/715* | (2006.01) |
| *A61K 45/06* | (2006.01) |
| *A61K 31/351* | (2006.01) |

(52) U.S. Cl.
CPC ............ *C08B 37/006* (2013.01); *A23L 1/296* (2013.01); *A61K 31/351* (2013.01); *A61K 31/715* (2013.01); *A61K 36/39* (2013.01); *A61K 45/06* (2013.01); *C07D 407/12* (2013.01); *C07D 407/14* (2013.01); *C07H 15/04* (2013.01)

(58) Field of Classification Search
None
See application file for complete search history.

(56) References Cited

U.S. PATENT DOCUMENTS

2009/0104295 A1    4/2009    Kohno

FOREIGN PATENT DOCUMENTS

| EP | 2548565 | * | 1/2013 | ............ A61K 36/39 |
| KR | 10-2008-0032127 A | | 4/2008 | |
| KR | 10-0988510 B1 | | 10/2010 | |
| WO | WO 2011/102690 | * | 8/2011 | ............ A61K 36/39 |

OTHER PUBLICATIONS

Asano et al., "Dihydroxynortropane alkaloids from calystegine-producing plants" Phytochemistry (2001) vol. 57 pp. 721-726.*
The Merck Manual of Diagnosis and Therapy, Seventeenth Edition, published 1999 by Merck Research Laboratories, pp. 165-177.*
Merriam-Webster's collegiate Dictionary, published 1998 by Merriam-Webster, incorporated, p. 924.*
Aiello, L., et al., "Vascular Endothelial Growth Factor in Ocular Fluid of Patients with Diabetic Retinopathy and Other Retinal Disorders", "New England Journal of Medicine", Dec. 1, 1994, pp. 1480-1487, vol. 331, No. 22.
Brownlee, M., et al., "Aminoguanidine Prevents Diabetes-Induced Arterial Wall Protein Cross-Linking", "Science", Jun. 27, 1986, pp. 1629-1632, vol. 232.
Brownlee, M., et al., "Advanced Glycosylation End Products in Tissue and the Biochemical Basis of Diabetic Complications", "New England Journal of Medicine", May 19, 1988, pp. 1315-1321, vol. 318, No. 20.
Defronzo, R., et al., "Pathogenesis of NIDDM: A Balanced Overview", "Diabetes Care", Mar. 1992, pp. 318-368, vol. 15, No. 3.
Lopez, P., et al., "Transdifferentiated Retinal Pigment Epithelial Cells Are Immunoreactive for Vascular Endothelial Growth Factor in Surgically Excised Age-Related Macular Degeneration-Related Choroidal Neovascular Membranes", "Investigative Ophthalmology and Visual Science", Apr. 1996, pp. 855-868, vol. 37, No. 5.
Pe'er, J., et al., "Hypoxia-induced expression of vascular endothelial growth factor by retinal cells is a common factor in neovascularizing ocular diseases", "Lab Invest", Jun. 1995, pp. 638-645 (Abstract Only), vol. 72, No. 6.

(Continued)

*Primary Examiner* — Eric Olson
(74) *Attorney, Agent, or Firm* — Vorys, Sater, Seymour & Pease LLP; Mih Suhn Koh

(57) ABSTRACT

The present invention relates to a novel compound isolated from *Quamoclit* sp., and more particularly to a novel compound isolated from *Quamoclit* sp. and a composition for preventing or treating diabetes and its complications comprising the compound as an active ingredient. The novel compound isolated from *Quamoclit* sp. according to the present invention has excellent effects on lowering blood sugar, promoting insulin secretion, inhibiting VEGF expression, and so on. Thus, the present invention not only functions to prevent or treat diabetes and its complications, but also functions to promote treatment effects when treated together with conventional diabetes medicines.

12 Claims, 20 Drawing Sheets

(56) References Cited

OTHER PUBLICATIONS

Smith, P., et al., "Mechanism of the degradation of non-enzymatically glycated proteins under physiological conditions: Studies with the model fructosamine, N epsilon-(1-deoxy-D-fructos-1-yl)hippuryl-lysine", "Eur. J. Biochem.", Dec. 1992, pp. 729-739, vol. 210, No. 3.

Vinson, J., et al., "Inhibition of Protein Glycation and Advanced Glycation End Products by Ascorbic Acid and Other Vitamins and Nutrients", "Nutritional Biochemistry", Dec. 1996, pp. 659-663, vol. 7.

Yokozawa, T., et al., "Effects of Oriental medicines on the production of advanced glycation endproducts", "Journal of Traditional Medicines", Jun. 2001, pp. 107-112, vol. 18, No. 3.

* cited by examiner ically glycated proteins may lose their function or may produce toxic substances, resulting in the occurrence of diabetic complications. —-- COMPOUND ISOLATED FROM QUAMOCLIT, AND COMPOSITION FOR PREVENTING OR TREATING DIABETES CONTAINING THE COMPOUND AS AN ACTIVE INGREDIENT

CROSS-REFERENCE TO RELATED APPLICATIONS

This application is a U.S. national phase under the provisions of 35 U.S.C. §371 of International Patent Application No. PCT/KR12/05129 filed Jun. 28, 2012, which in turn claims priority of Korean Patent Application No. 10-2011-0082445 filed Aug. 18, 2011 and Korean Patent Application No. 10-2012-064524 filed Jun. 15, 2012. The disclosures of such international patent application and Korean priority patent applications are hereby incorporated herein by reference in their respective entireties, for all purposes.

TECHNICAL FIELD

The present invention relates to a novel compound isolated from *Quamoclit* sp. and a composition comprising thereof as an active ingredient, and more particularly to a novel compound isolated from *Quamoclit* sp. and a composition for preventing or treating diabetes and its complications comprising the compound as an active ingredient.

BACKGROUND ART

Diabetes refers to a group of metabolic disorders characterized by chronic hyperglycemia resulting from defects in insulin secretion or action. When abnormally high blood glucose levels are continued for a long period time, various complications occur due to chronic metabolic disorders and the result chronic vascular injuries.

Diabetes, a typical adult metabolic disease, is suffered by about 5% of the population in the world and causes a huge loss of lives and properties. Most diabetic patients take oral therapeutic agents, but a safe therapeutic agent has not yet been developed. Insulin resistance is known to be the most important cause of diabetes, but the exact mechanism of diabetes is still unknown, and it is known that diabetes is caused by genetic predisposition and environmental factors. Diabetes is the third leading cause of death in the world, and the number of diabetic patients in 2010 is estimated to be about 250 millions. In Korea, the number of diabetic patients is expected to increase continuously in the future. Non-insulin dependent diabetes (NIDDM) is the seventh leading cause of death in Korea and accounts for more than 90% of diabetic patients. It is called "adult diabetes", because it occurs mainly in persons who are over 40 years old. It is a metabolic disorder which is caused by the insufficient production or inappropriate use of insulin (DeFronzo R A et al., Diabetes Care, 15:318, 1992). Although the cause of onset of NIDDM is not yet clearly known, it is believes that NIDDM is caused by environmental factors, including westernized eating habits and life styles, as well as genetic factors such as obesity and lack of exercise. For treatment of NIDDM, dietary therapy and exercise therapy are first attempted, and if the therapeutic effects of such therapies are insufficient, drugs are used, and in many cases, insulin is used. Insulin is required for patients whose blood glucose levels are not regulated by dietary therapy and oral blood glucose lowering drugs. However, because insulin is a protein, it is inactivated by hydrolysis in the stomach. For this reason, it cannot be administered orally and should be injected intravenously or subcutaneously.

Oral blood glucose lowering drugs improve the sensitivity of insulin receptor of a cell and stimulate the pancreases to promote secretion of insulin, and thus they are used to regulate blood glucose levels in NIDDM patients. However, oral therapy for treatment of NIDDM can cause hypoglycemia, nausea, vomiting, diarrhea, eruption and the like. Particularly, it can cause serious adverse effects such as fatal lactic acidosis. In addition, oral blood glucose lowering agents, when used for a long time, cause cardiovascular disorders or gastrointestinal and hepatic disorders. For this reason, the long-term use thereof is not recommended. Due to such shortcomings and adverse effects, among current therapeutic drugs, there are little or no drugs, which show satisfactory effects, have high safety without adverse effects and can be applied to all diabetic patients. Thus, there is an urgent need to develop a more efficient drug for treating diabetes, particularly NIDDM.

About 10 years after the onset of diabetes, almost all the organs of the body are damaged, causing complications. Such complications include acute diseases, such as hypoglycemia, ketoacidosis, hyperosmolar nonketotic hyperglycemia, hyperglycemic coma, and diabetic ketoacidosis; and chronic diseases, such as diabetic retinopathy, diabetic cataract, diabetic nephropathy, diabetic neuropathy, cardiovascular complications, and viral infections. Chronic diabetic nephropathy is the most important cause of hemodialysis and end-stage renal failure, and diabetic cataract causes blindness, and eventually leading to death.

The mechanisms causing diabetes are generally described by nonenzymatic glycation of proteins, polyol pathways, and the like. The non-enzymatic glycation of protein is caused by condensation of amino acid group such as lysine residue of protein with reduced sugar without enzymatic action, that is, the Maillard reaction. As a result of the reaction, glycation end products are produced. The non-enzymatic glycation of protein includes two steps. In the first step, an amino acid group (such as lysine of protein) and aldehyde or ketone of reduced sugar are subjected to a nucleophilic addition reaction without enzymatic action to form a Schiff base, a product of the early stage, and the Schiff base is condensed with the adjacent ketoamine adduct to produce a reversible Amadori-type early glycation product. In the second step, as the high blood glucose level is kept, the reversible Amadori type early glycation product is rearranged without degradation and is cross-linked with a protein to form irreversible advanced glycation end products.

Unlike the reversible Amadori type early glycation product, the advanced glycation end products are irreversible products. Therefore, the advanced glycation end products are not degraded, even when the blood glucose level is returned to the normal level, but they are accumulated in tissue to abnormally change the structure and function of the tissue for the survival period of the protein, thus causing complications in the tissue (Vinson, J. A. et al., *J. Nutritinal*

Biochemistry, 7: 559, 1996; Smith, P. R. et al., Eur. J. Biochem., 210:729, 1992). For example, glycated albumin which is one of the advanced glycation end products produced by the reaction of glucose with various proteins acts as the major cause of chronic diabetic nephropathy. The glycated albumin is more easily introduced into glomerular cells compared to normal albumin, and a high concentration of glucose stimulates mesangial cells to increase the synthesis of extracellular matrix. The excessively introduced glycated albumin and the increased extracellular matrix cause the fibrosis of glomeruli. By these mechanisms, the glomeruli are continuously damaged, so that extreme treatments such as hemodialysis and organ transplantation are necessarily required. In addition, it was reported that, in the case of chronic diabetes, the collagen in arterial walls and the basement membrane protein in glomeruli bind to the advanced glycation end products and are accumulated in tissue (Brownlee, M. et al., Sciences, 232:1629:1986).

Due to the non-enzymatic protein glycation as described above, proteins such as the basement membrane, plasma albumin, the crystalline lens protein, fibrin, collagen and the like are glycated. The advanced glycation end products abnormally change the structure and function of the tissue to cause chronic diabetic complications such as diabetic retinopathy, diabetic cataract, diabetic nephropathy, diabetic neuropathy and the like (Yokozawa, T. et al., J. of Trad. Med., 18:107, 2001). Thus, it was found that inhibiting the formation of advanced glycation end products is very important in delaying the onset of diabetic complications or preventing or treating diabetic complications (Brownlee, M. et al., N. Engl. Med., 318:1315, 1988).

In addition, advanced glycation end products overexpress vascular endothelial growth factor (VEGF) mRNA and protein to cause non-proproliferative or proliferative diabetic retinopathy. Aberrant angiogenesis or the pathogenic growth of new blood vessels is involved in a number of conditions. Such conditions include diabetic retinopathy, psoriasis, exudative or wet age-related macular degeneration (ARMD), rheumatoid arthritis and other inflammatory diseases, and most cancers (Aiello et al., New Engl. J. Med, 331:1480, 1994; Peer et al. Lab. Invest., 72:638, 1995). The VEGF in tumors or tissues suffering from diseases associated with these conditions expresses at an aberrantly high level, and has increased angiogenesis or vascular permeability. ARMD in particular is a clinically important angiogenic disease. This condition is characterized by choroidal neovascularization in one or both eyes in aging individuals, and is the major cause of blindness in industrialized countries. Anti-angiogenic agents used in various therapies can produce only a stoichiometric reduction in VEGF or VEGF receptor, and the agents are typically overwhelmed by the abnormally high production of VEGF by the diseased tissue (Lopez et al., Invest. Opththalmol. Vis. Sci., 37:855, 1996).

Accordingly, the present inventors have made extensive efforts to find a natural herbal substance for treating diabetes and its complications, which has less adverse effects. As a result, the present inventors have found that a novel compound isolated from Quamoclit sp. functions to improve diabetic indexes such as blood sugar, glycated hemoglobin, urine protein, etc. in diabetes mice, thereby completing the present invention.

DISCLOSURE OF INVENTION

Technical Problem

It is an object of the present invention to provide a novel compound, which has less adverse effects, isolated from a natural herbal substance for treating diabetes and its complications.

Another object of the present invention is to provide a pharmaceutical composition for preventing or treating diabetes and its complications, which contains the novel compound as an active ingredient.

Technical Solution

To achieve the above object, the present invention provides a compound of chemical formula 1:

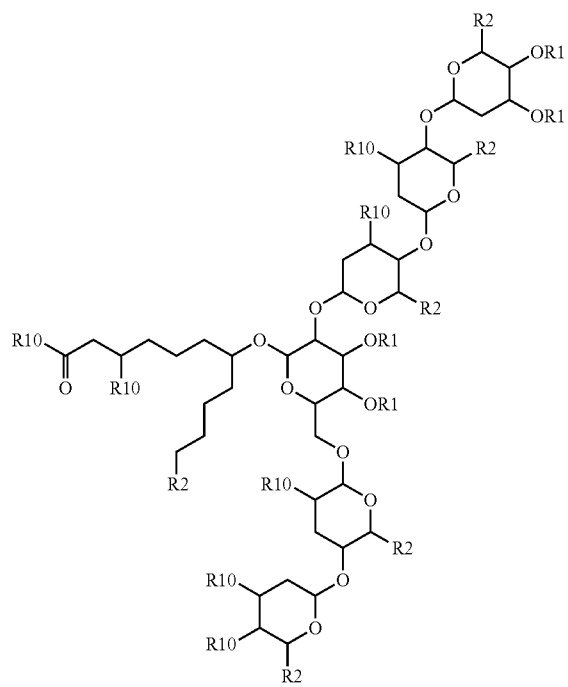

[Chemical formula 1]

wherein R1 and R2 are independently hydrogen, $C_{1-20}$ alkyl group, $C_{6-30}$ aryl group, $C_{1-20}$ allyl group, $C_{6-30}$ arylalkyl group or acyl group.

The present invention also provides a method for preparing a compound of chemical formula 2, the method comprising the steps of: (a) extracting Quamoclit sp. with a solvent selected from the group consisting of water, alcohol, an organic solvent, and mixtures thereof, thereby preparing Quamoclit extract; (b) suspending the Quamoclit extract by adding water thereto, and fractionating with normal hexane, ethyl acetate and butanol, thereby obtaining water fraction; and (c) isolating and purifying the water fraction, thereby obtaining the compound of chemical formula 2;

[chemical formula 2]

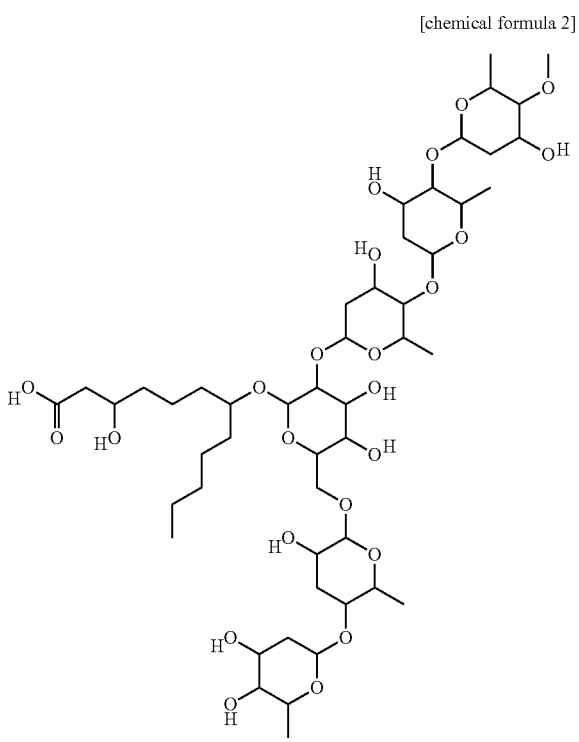

The present invention also provides a pharmaceutical composition for preventing or treating diabetes and its complications, which contains a compound of chemical formula 1; salt thereof; or extracts comprising a compound of chemical formula 1 or salt thereof, as an active ingredient.

The present invention also provides a health functional food for preventing diabetes and its complications, which contains a compound of chemical formula 1; salt thereof; or extracts comprising a compound of chemical formula 1 or salt thereof, as an active ingredient.

The present invention also provides a method of treating diabetes and its complications, by administering to a subject in need thereof a pharmaceutical composition comprising a compound of chemical formula 1; salt thereof; or extract comprising a compound of chemical formula 1 or salt thereof, as an active ingredient.

The present invention also provides a method of preventing diabetes and its complications, by administreing to a subject in need thereof a health functional food comprising a compound of chemical formula 1; salt thereof; or extract comprising a compound of chemical formula 1 or salt thereof, as an active ingredient.

BEST MODE FOR CARRYING OUT THE INVENTION

Figure 1:
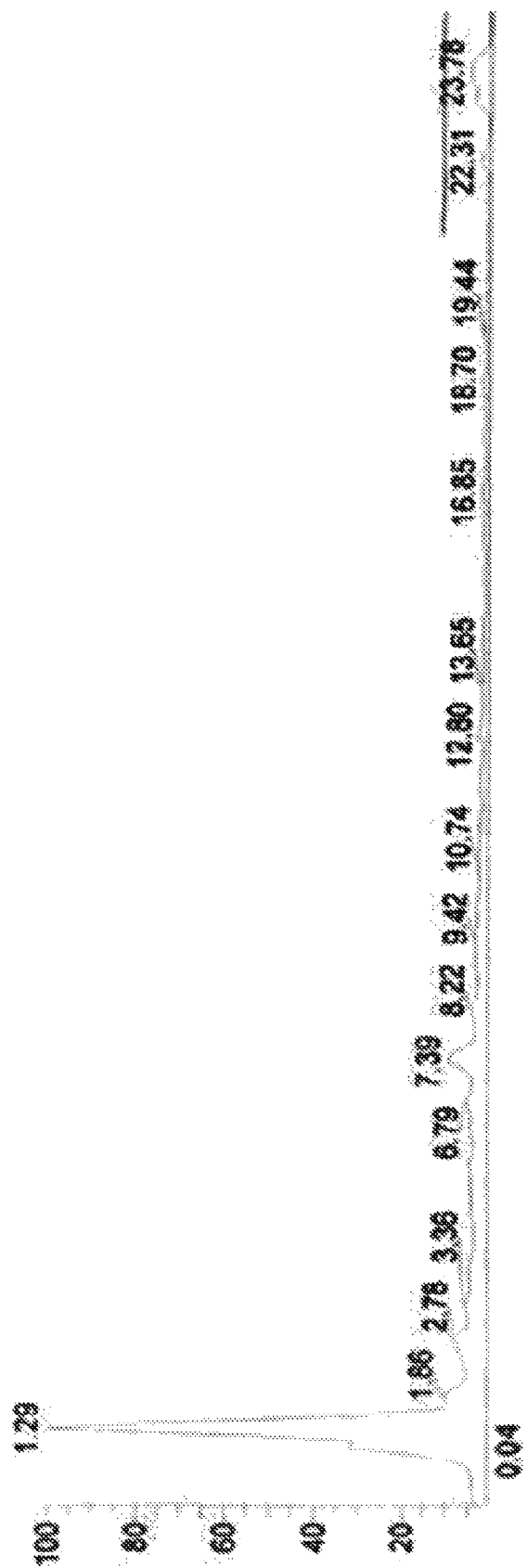
FIG. 1 is HPLC spectrum of a novel compound isolated from *Quamoclit angulata*.

In one aspect, the present invention is directed to a compound of chemical formula 1:

[chemical formula 1]

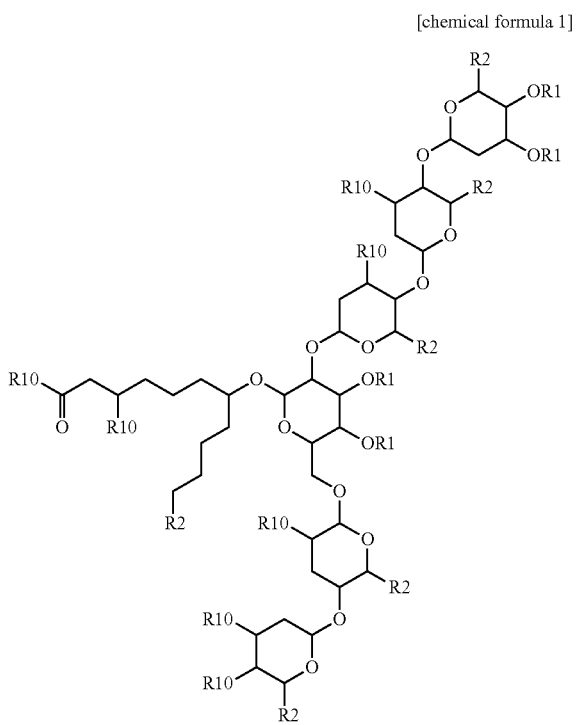

wherein R1 and R2 are independently hydrogen, $C_{1-20}$ alkyl group, $C_{6-30}$ aryl group, $C_{1-20}$ allyl group, $C_{6-30}$ arylalkyl group or acyl group.

Preferably, the R1 and R2 of chemical formula 1 may be independently hydrogen or $C_{1-20}$ alkyl group.

More preferably, the compound of chemical formula 1 may comprise a structure of chemical formula 2:

[chemical formula 2]

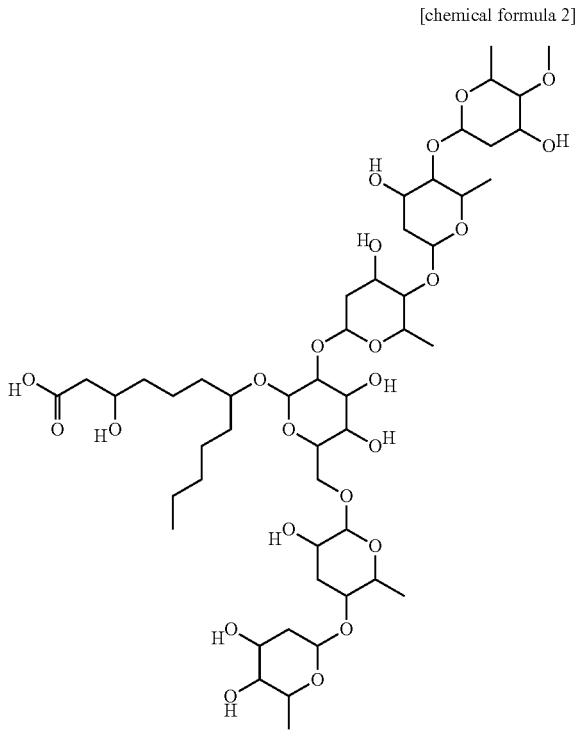

Also, the compound of chemical formula 1 may be derived from *Quamoclit* sp., and preferably derived from *Quamoclit angulata*. *Quamoclit angulata* that is used in the present invention is a annual vine plant belonging to the family Convolvulaceae of the order Tubiflorae. It is native to tropical Africa and is cultivated mainly for ornamental purposes. It is characterized in that the vines grow similar to a morning glory and are rolled up on the left side. The whole plant has a length of about 3 m. The leaves are alternate with long petioles and are heartes shaped. The tips of a leaf are acute and the both ends of the lower region in the leaf are pointed. The flowers bloom between August and September and are yellowish red, and 3-5 flowers are suspended from each stalk. The flower resemble the appearance of a morning glory and has 5 sepals, 5 stamens and 1 pistil. The fruit is capsular, ripens in September and has a sepal remaining thereon. This plant is similar to *Quamoclit coccinea*, but the leaf is not divided.

The compound which contains a structure of chemical formula 2 according to the present invention is a novel compound isolated from *Quamoclit* sp., has an elemental chemical formula of $C_{49}H_{88}O_{24}$, is a kind of resin glycoside having a structure of chemical formula 1, and sugar structure such as beta-D-fucopyranose and the like is linked thereto.

In the present invention, the compound of chemical formula 2 is named as KRIBB-BH-P. The novel compound is bright yellow color powder. LC-MS result of the compound shows molecular ion m/z 1059.4, 916.4(1052.4−145), 786.9(916.4−136), 514.8(786.9−136), 378.9(514.8−136), 232.9(378.9−146), and the result is consistent with the elemental chemical formula of $C_{49}H_{88}O_{24}$. Additionally, NMR assignment is completed through 1D-NMR (H-NMR, C-NMR).

A novel compound according to the present invention can be prepared using a known method. For example, the compound can be extracted with a solvent selected from among water, an alcohol, an aqueous alcohol solution, an organic solvent, and mixtures thereof. Preferably, the compound may be extracted using water or alcohol. In addition, the compound can be purified using activated carbon.

The compound of chemical formula 2 can be prepared by the following method. In another aspect, the present invention is directed to a method for preparing a compound of chemical formula 2, the method comprising the steps of: (a) extracting *Quamoclit* sp. with a solvent selected from the group consisting of water, alcohol, an organic solvent, and mixtures thereof, thereby preparing *Quamoclit* extract; (b) suspending the *Quamoclit* extract by adding water thereto, and fractionating with normal hexane, ethyl acetate and butanol, thereby obtaining water fraction; and (c) isolating and purifying the water fraction, thereby obtaining the compound of chemical formula 2.

In the step (a), preferably, *Quamoclit* is dried, and *Quamoclit* extract is primarily isolated and purified using carbon-packed column. The method for isolating and purifying in the step (c) can be, but not limited to, for example, chromatography.

In one aspect of the present invention, the compound of chemical formula 2 was prepared by the following manner. 51 g of crushed *Quamoclit angulata* was extracted with a solvent selected from the group consisting of water, alcohol, an organic solvent, and mixtures thereof, in an ultrasonic extractor at room temperature for 15 minutes at 2-hr intervals for 2-3 days or hot water extracted with a solvent of water at 50° C. The resulting extract was extracted under reduced pressure in a rotary vacuum evaporator at room temperature, and the concentrator was dried in a vacuum freeze dryer and then dissolved in water, thereby obtaining a *Quamoclit angulata* extract.

The obtained *Quamoclit angulata* extract was passed through an activated carbon-packed column to absorb the active components thereof onto the activated carbon. Then, the activated carbon-packed column was washed with distilled water to remove non-adsorbed components. Then, to the activated carbon-packed column from which the non-adsorbed components have been removed, an organic solvent such as 10-50% (v/v) ethanol was added while increasing the concentration continuously or stepwise, so that the active components of *Quamoclit angulata* adsorbed onto the activated carbon were purified by elution. Then, the *Quamoclit angulata* extract was collected. The *Quamoclit angulata* extract purified as described above was concentrated under reduced pressure in a rotary vacuum evaporator at room temperature, and the concentrated extract was freeze-dried in a vacuum, and then dissolved in water, thereby obtaining an aqueous solution of a *Quamoclit angulata* extract.

The aqueous solution of a *Quamoclit angulata* extract was suspended with distilled water, and then fractionated with n-hexane, ethyl acetate (EtOAc) and butanol (BuOH) in order, thereby obtaining n-hexane fractions, EtOAc fractions, BuOH fractions and water fractions, respectively.

Using the solvent fractions, respectively, inhibition experiments of VEGF production were performed. The water fraction which showed the most excellent efficacy was divided into 10 fractions through column chromatography using silica gel as a stationary phase and Aetonitril-water mixture solvent (1:9→9:1 v/v) as a mobile phase, and Sephadex column chromatography (5.0×65 cm, MeOH) was performed of ACN20 [elution with Acertonitril-DW (2:8 v/v)], thereby purifying a novel compound.

In one Example of the present invention, when the novel compound isolated from *Quamoclit angulata*, KRIBB-BH-P was injected into diabetic mice, it was demonstrated that diabetic indexes such as blood sugar, glycated hemoglobin, and the constitution of urine protein were improved.

In addition, when the novel compound isolated from *Quamoclit angulata*, KRIBB-BH-P was injected into diabetic mice, it was demonstrated that there was no hepatotoxicity or disorder of liver function. Thereby it was demonstrated that the application of KRIBB-BH-P in vivo is safe.

In another Example of the present invention, when the novel compound isolated from *Quamoclit angulata*, KRIBB-BH-P was injected into diabetic mice, it was demonstrated that adiponectin levels were increased, and thereby insulin resistance was improved. Also, it was demonstrated that glucagon levels became normal, which was abnormally increased in diabetic mice.

In another aspect, the present invention is directed to a pharmaceutical composition for preventing or treating diabetes and its complications or a health functional food for preventing diabetes and its complications, which contains a compound of chemical formula 1; salt thereof; or extracts comprising a compound of chemical formula 1 or salt thereof, as an active ingredient.

In the present invention, preferably, the R1 and R2 of chemical formula 1 may be independently hydrogen or $C_{1-20}$ alkyl group. More preferably, the compound of chemical formula 1 may comprise a structure of chemical formula 2.

In the present invention, the pharmaceutical composition and the health functional food can further comprises an extract obtained by plant-culturing or tissue-culturing.

The novel compound of the present invention can prevent or treat not only diabetes, but also diabetic complications, but not limited to, which are selected from the group consisting of hyperglycemia, hyperinsulinemia, insulin resistance, dyslipidemia, impaired fasting glucose, impaired glucose tolerance, obesity, arteriosclerosis, microangiopathy, renal disease, heart disease, foot ulcer, arthritis, osteoporosis, and ophthalmologic disease induced by diabetes.

As used herein, the term "diabetes" is intended to include all types of diabetes, including type 1 diabetes, type 2 diabetes, adult diabetes occurring in young persons, latent autoimmune diabetes, and pancreatic diabetes, as well as diabetic complications, including not only the above examples but also glomerulosclerosis, impotence, diabetic neuropathy, premenstrual syndrome, restenosis, ulcerative colitis, coronary heart disease, high blood pressure, angina pectoris, myocardial infarction, stroke, disease of skin and connective tissue, metabolic acidosis, symptoms from poor glucose tolerance, etc.

As used herein, the term "ocular diseases" is intended to include, in addition to diabetic retinopathy, all ocular diseases caused by diabetes, including a cataract, macular degeneration, external ophthalmoplegia, iridocyclitis, neuritis, glaucoma, retinal degeneration, fundus hemorrhage, ametropia, subconjunctival hemorrhage, and vitreous haemorrhage.

The pharmaceutical composition of the present invention contains a novel compound isolated from *Quamoclit* as an active ingredient, and may be provided as a pharmaceutical composition containing the novel compound alone or in combination with at least one pharmaceutically acceptable carrier, excipient or diluent.

In addition, the pharmaceutical composition of the present invention may also be used in combination with an agent for treating diabetes or its complications, known in the art. Namely, the pharmaceutical composition of the present invention may also be administered with compounds having an effect on preventing or treating diabetes and its complications known in the art.

Therefore, the pharmaceutical composition of the present invention may further comprise an anti-diabetic compound, known in the art.

The antidiabetic compound is selected from, but not limited to, the group consisting of nateglinide, repaglinide, glitazones, sulfonylureas, metformin, glimepiride, thiazolidinediones, biguanides, acarbose which is α-glucosidase inhibitor, and prandin of meglitinides.

In the present invention, the administration manner of the pharmaceutical composition, but not limited to, includes oral, intravenous, intramuscular, intracoronary, intrabone-marrow, intradural, intracardiac, dermal, subcutaneous, intraperitoneal, intranasal, enteral, local, sublingual and rectal administration.

Oral and parenteral administration is preferable. As used herein, the term "parenteral" is intended to include subcutaneous, intradermal, intravenous, intramuscular, intraarticular, intrabursa, intrasternum, intradural, intrafocal and intracranial injection or implantation techniques.

The pharmaceutical composition of the present invention can be a form of formulation for injection as a water or oil suspension for sterilized injection. The suspension can be prepared using an appropriate dispersing agent, a wetting agent (for example, Twin 80), or an suspending agent, by the known art in the field of the present invention. The formulation for injection may be a formulation for injection or a suspension (for example, 1,3-butandiol solution), in nontoxic and parenterally acceptable, a diluents or a solvent. There are mannitol, water, Ringer's solution, isotonic sodium chloride solution as an acceptable vehicle and solvent. In addition, sterilized non-volatile oil is commonly used as a solvent or a suspending medium. Any non-volatile oil which comprises synthetic mono- or di-glyceride and thus less irritation can be used. Natural oils which fatty acids such as oleic acid and its derivatives are acceptable (for example, olive oil or castor oil), specifically those polyoxyethylated, are useful for a formulation for injection.

The pharmaceutical composition of the present invention can be orally administrated as any form which is orally acceptable, but not limited to, including capsules, tablets, water suspension and solution. In case of tablets for oral administration, as commonly used carriers, lactose and corn starch are included. Lubricants such as magnesium stearate can be typically added. In case of capsules for oral administration, as useful diluents, lactose and corn starch are included. When water suspension is orally administrated, an active ingredient is mixed with emulsifiers and suspending agents. In case needed, a sweeting agent and/or a flavoring agent and/or a coloring agent can be added.

The pharmaceutical composition of the present invention also can be administrated as a suppository form for rectal administration. The pharmaceutical composition can be prepared by mixing the compound of the present invention with non-irritating diluting agents which is solid at a room temperature and liquid at rectal temperature. The diluting agents include, but not limited to, cocoa butter, beeswax and polyethylene glycol.

Oral administration of the pharmaceutical composition of the present invention is especially useful, when a targeted treatment is related to region or organ which is easy to access by local administration. In case of local administration to skin, the pharmaceutical composition need to be prepared as a proper ointment comprising an active ingredient suspended or dissolved in a carrier. The carrier for local administration of the compound of the present invention includes, but not limited to, mineral oil, liquid paraffin, white vaseline, propylene glycol, polyoxyethylene, polyoxypropylene compound, oil wax and water. As another manner, the pharmaceutical composition of the present invention can be prepared as a proper lotion or cream comprising an active ingredient suspended or dissolved in a carrier. The carrier for local administration of the compound of the present invention includes, but not limited to, mineral oil, sorbitan monostearate, polyxorbate 60, cetyl ester wax, cetearyl alcohol, 2-octyldodecanol, benzyl alcohol and water. The pharmaceutical composition of the present invention also can be locally applied by rectal suppository or enemata clyster through lower gasterointestine. Transdermal patch which is locally applied is included in the present invention. The pharmaceutical composition of the present invention can be administrated by intranasal aerosol or inhalation. The composition can be prepared by the known art in the field of pharmacy, and can be prepared using a preserved agent such as benzyl alcohol, an absorption enhancer for increasing bioavailability, fluorocarbon and/or well-known solubilizing agent, or a dispersing agent, as a solution in salt water.

In the pharmaceutical composition of the present invention, the novel compound of the present invention is comprised at a therapeutically or preventively effective amount.

However, a specific amount for a specific patient may change according to several reasons including activity of used specific compound, age, weight, general health, sex, diet, administration time, administration manner, emission rate, drug mix and specific disease which will be prevented or treated. The pharmaceutical composition of the present invention can be prepared as a pellet, a sugar-coated tablet, a capsule, a liquid formulation, gel, syrup, slurry or a suspension.

In case of administration of the pharmaceutical composition of the present invention into a subcutaneous cell from fish, the pharmaceutical composition can be administrated into branchial pouch or digestive duct. The pharmaceutical composition of the present invention can be injected into a muscle cell or other cell in a muscle tissue, and can be injected into a visceral cell in an abdominal cavity.

Preferably, the pharmaceutical composition for oral administration can be prepared by mixing with solid diluting agent and active ingredients together, and can be prepared as a granulate form to prepare as a tablet or a sugar-coated tablet. The proper diluting agent includes sugar form such as lactose, sucrose, mannitol and sorbitol, gums including starch from corn, flour, rice, potato or other plant, cellulose such as methyl cellulose, hydroxypropylmethyl-cellulose or sodium carboxymethylcellulose, arabic gum, tragacanth gum, protein filler including carbohydrate, gelatin, collagen. In case needed, a disintegrating agent or a solvent of a salt form like cross-linked polyvinylpyrrolidone, agar, alginic acid, or sodium alginic acid can be added.

In case of parental administration, the pharmaceutical composition can be prepared as an aqueous solution. Preferably, physically appropriate buffer such as Hank's solution, Ringer's solution, or physically buffered salt water can be used. In case of an aqueous injection suspension, substrates which can increase viscosity of suspension like sodium carboxymethyl cellulose, sorbitol, or dextran, can be added. In addition, a suspension of an active ingredient can be prepared as an oily injection suspension. Proper lipophilic solvent or carrier includes fatty acid as sesame oil, and synthetic fatty acid ester as ethyl olate, triglyceride or liposome. Polycationic amino polymers can be used as a carrier. Randomly, proper stabilizers or drugs can be used to increase the solubility of the compound and prepare highly concentrated solution.

The health functional food of the present invention can be prepared as a form of food for preventing or improving diabetes and its complications. The health functional food of the present invention is a food composition, and examples thereof include all types of food including functional food, nutritional supplement, health food, and food additives. The types of food mentioned above may be prepared in various forms by conventional methods known in the art. For example, for the health food, the novel compound isolated from *Quamoclit* of the present invention may be prepared in the form of tea, juice and drink, or it may be granulized, encapsulated or powdered. Also, the functional food may be prepared by adding the novel compound isolated from *Quamoclit* of the present invention to beverages (including alcoholic beverage), fruits and processed foods thereof (e.g., canned fruit, bottled food, jam, marmalade, etc.), fishes, meats and processed foods thereof (e.g., ham, sausage, corn beef, etc.), bread and noodles (e.g., Japanese noodle, buckwheat noodles, ramen, spaghetti, macaroni, etc.), fruit juice, various drinks, cookies, taffy, milk products (e.g., butter, cheese, etc.), edible plant oil and fat, margarine, vegetable proteins, a retort food, frozen food, various seasonings (e.g., soybean paste, soy sauce, sauces, etc.) and the like.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Isolation of Novel Compound from *Quamoclit angulata*

51 g of *Quamoclit angulata* collected in Seogwang-ri, Andeok-myeon, Seogwipo-si, Jeju-do, Korea was extracted by hot water extraction using water as a solvent at 50° C. or by a sound wave extractor using a solvent selected from a group consisting of water, alcohol, an organic solvent, and a mixed solution thereof every 2 hours for 15 minutes over two to three days at room temperature. After the thus-obtained extract was concentrated by rotary vacuum evaporator under reduced pressure at room temperature, the extracted residue was dried by a vacuum freezer dryer and a dried extract of *Quamoclit angulata* was obtained. The concentration was suspended in water and passed through column chromatography filled with activated carbon to adsorb effective component of the *Quamoclit angulata* and a column filled with activated carbon was washed with distilled water, thereby removing non-adsorbed component. An organic solvent such as 10~50%(v/v) ethanol, and the like, was supplied into the activated carbon-filled column from which the non-adsorbed component is removed while increasing concentration thereof in a continuous scheme or in stages to thereby elute, isolate and refine the effective component of the *Quamoclit angulata* adsorbed onto the activated carbon, thereby obtaining a *Quamoclit angulata* extract. The isolated and refined *Quamoclit angulata* extract was concentrated under reduced pressure, water was added to 5 g of the concentrated *Quamoclit angulata* extract, thereby dissolving the *Quamoclit angulata* extract so as to have a concentration of 20 mg/ml.

The water extract was suspended in distilled water, followed by sequential solution fraction with normal hexane (n-hexane), ethyl acetate (EtOAc), and butanol (BuOH), thereby obtaining n-hexane fraction, EtOAc fraction, BuOH fraction, and water fraction, respectively.

Each of the solvent fractions was subjected to Vascular Endothelial Growth Factor (VEGF) inhibition experiment, and among them, water fraction having the most excellent efficiency was divided into 10 fractions by column chromatography having C18 reverse phase silica gel as a stationary phase and acetonitrile-water mixed solvent (1:9→9:1 v/v) as a mobile phase. Among them, the fraction ACN 20 [MeOH-water (1:9 v/v) elution] was subjected to Sephadex column chromatography (5.0×65 cm, MeOH), thereby refining a novel compound (FIG. 1). Conditions and result used in the above-described experiment was follows:

High Performance Liquid Chromatography (HPLC) Analysis (Shimadzu Model)
Column: C18 Reverse Phase Column
Mobile Solvent: 90% Methanol
Flow Rate: 1 ml/min
Residence Time: 1.29 Minutes.

Example 2

Confirmation of Structure of *Quamoclit angulata*-Derived Novel Compound

Figure 2:
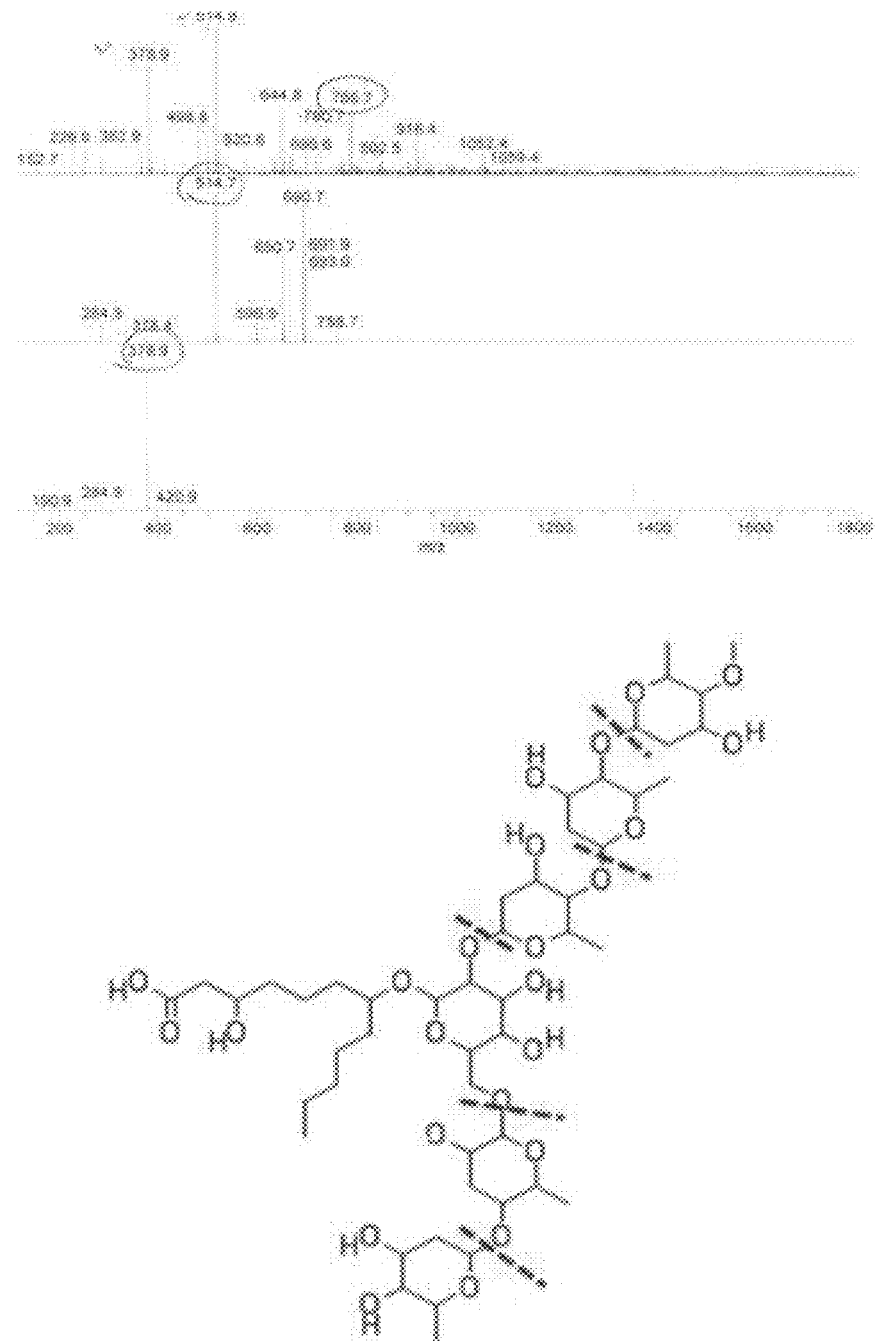
FIG. 2 is LC-MS spectrum of a novel compound isolated from *Quamoclit angulata*.

The novel compound isolated in Example 1 above was a pale yellow powder, and had molecular ion m/z of 1059.4, 916.4(1052.4−145), 786.9(916.4−136), 514.8(786.9−136), 378.9(514.8−136) and 232.9(378.9−146) detected by LC-MS (FIG. 2), which was coincided with Molecular Formula (Elemental Formula) of $C_{49}H_{88}O_{24}$.

A NMR assignment was clearly completed by 1D-NMR (H NMR, C NMR).

Figure 3:
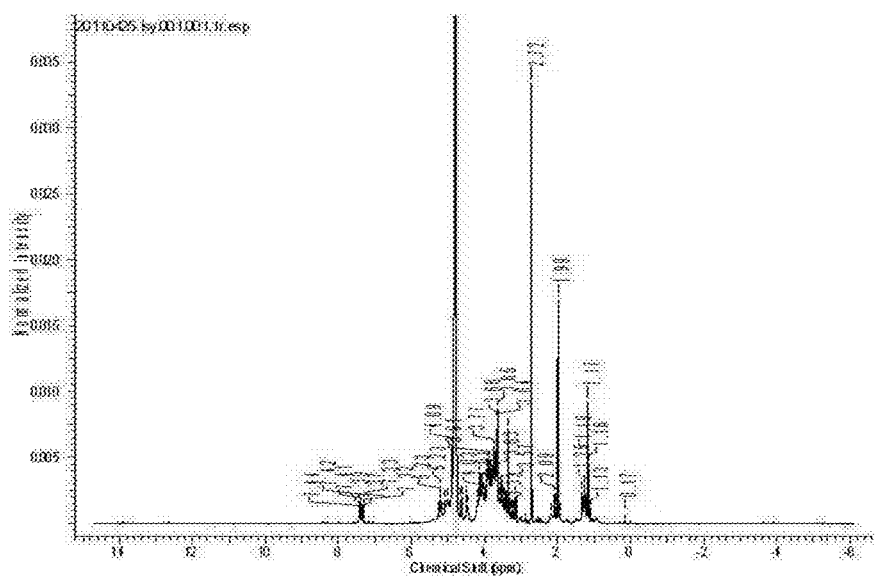
FIG. 3 is H-NMR spectrum of a novel compound isolated from *Quamoclit angulata* using $D_2O$ as a solvent.

Hydrogen nuclear magnetic resonance (H-NMR) result measured with water substituted with deuterium ($D_2O$) as a solvent and tetramethylsilane (TMS) as a standard material was shown in FIG. 3.

Figure 4:
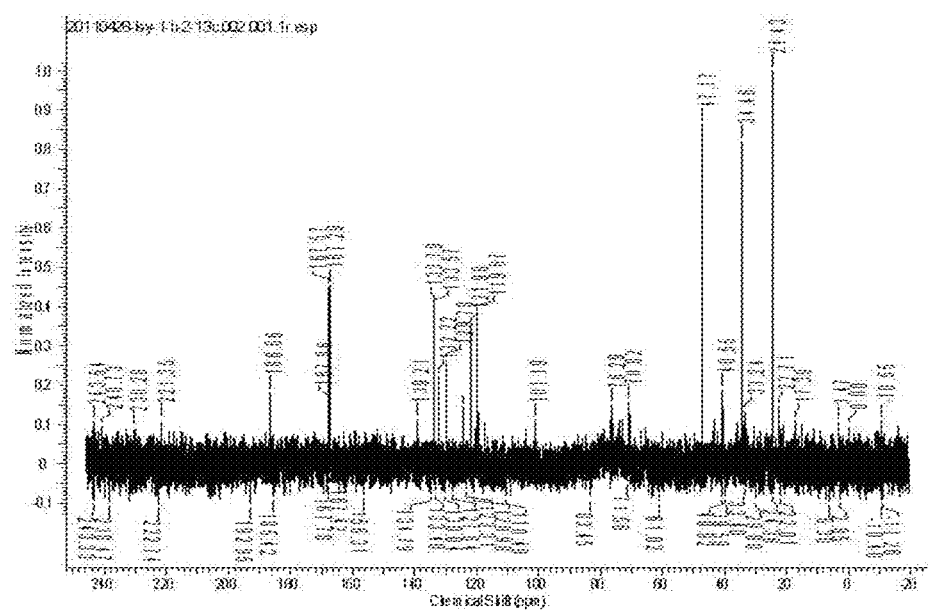
FIG. 4 is C-NMR spectrum of a novel compound isolated from *Quamoclit angulata* using $D_2O$ as a solvent.

Carbon nuclear magnetic resonance (C-NMR) result measured with water substituted with deuterium ($D_2O$) as a solvent and tetramethylsilane (TMS) as a standard material was shown in FIG. 4.

It was confirmed from the above results that the *Quamoclit angulata*-derived novel compound isolated by Example 1 above is a novel compound having Molecular Formula of $C_{49}H_{88}O_{24}$ and having a structure represented by the following [Chemical Formula 2]:

[Chemical Formula 2]

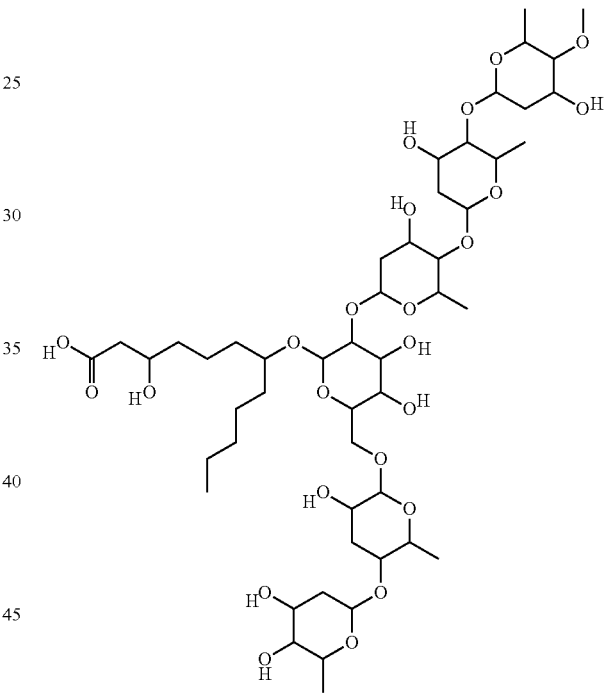

The compound has a structure with sugars linked to beta-D-fucopyranose as a kind of glucoside and is referred to as KRIBB-BH-P.

Example 3

Confirmation of VEGF Inhibition Activity of *Quamoclit angulata*-Derived Novel Compound In order to confirm inhibition activity of VEGF of the novel compound isolated from the *Quamoclit angulata* prepared in Example 1 above, ARPE 19 cell line which is human retinal pigment epithelium cell line was treated with the novel compound and expression of the VEGF protein inducting diabetic complications such as diabetic retinopathy, and the like was confirmed.

10% fetal bovine serum (FBS) was added to DMEM; F12 medium and ARPE 19 cell line (ATCC, USA) was cultured therein. In order to induce expression of the VEGF protein from ARPE 19 cell line, the cells were smeared on 60Φ plate at a concentration of 1×10$^5$ cell/plate, 10% FBS serum-free was added to DMEM low glucose medium, followed by culturing for 24 hours, the culture fluid was changed into a culture fluid containing 30 mM glucose in the DMEM low glucose medium, and the novel compound KRIBB-BH-P was added thereto so that a final concentration thereof was 0.5 μg/ml, followed by culturing for 72 hours in order to confirm production of VEGF protein. Here, a cell (− control group) in which the VEGF was not expressed by treatment with 5.5 mM glucose was set as reference which is a control group and a degree of VEGF expression (+ control group) by treatment with 30 mM glucose was confirmed, and comparison of VEGF expression inhibition activity of the *Quamoclit angulata*-derived compound was conducted. The 30 mM glucose used in the present experiment is a concentration under conditions that optimally induce expression of VEGF at each experiment.

The culture fluid of ARPE 19 cell cultured by the above-described method was obtained and an amount of the secreted VEGF was measured using VEGF ELISA kit (R&D, UK).

Figure 5:
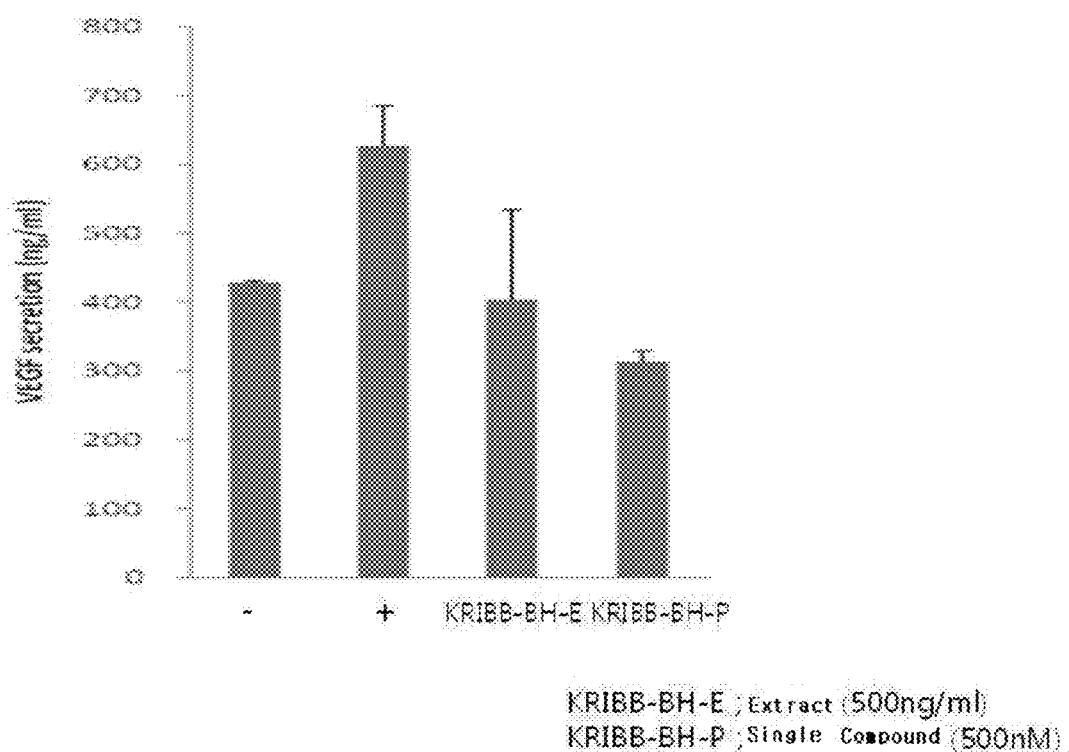
FIG. 5 is a graph showing the inhibition of VEGF protein production in human retinal epithelial cells by a novel compound isolated from *Quamoclit angulata*.

As a result, it was confirmed from FIG. 5 that VEGF expression was decreased in the experimental group treated with KRIBB-BH-P was treated.

Example 4

Confirmation of Insulin Secretion Acceleration of *Quamoclit angulata*-Derived Novel Compound An insulin secretion acceleration activity of the novel compound KRIBB-BH-P isolated from *Quamoclit angulata* was confirmed in Min 6 cell line which is a mouse pancreatic β cell tumor.

15% FBS was added to HDMEM medium and Min 6(ATCC, USA) was cultured therein. In order to induce insulin expression from Min 6 cell line, the cells were smeared on a 96 well plate at a concentration of 1×10$^4$ cell/plate, 15% FBS serum-free was added to DMEM high glucose medium, followed by culturing for 72 hours, washing with PBS buffer solution, and then culturing in HBSS buffer solution for 2 hours, the culture fluid was changed into HBSS buffer solution having 25 mM glucose added thereto, and the novel compound KRIBB-BH-P was added thereto so that a final concentration thereof was 0.5 ng/ml, followed by culturing for 2 hours in order to confirm whether or not the insulin expression was promoted. Here, an amount of insulin expression in cell in which insulin expression was not induced by treatment with 5.5 mM glucose was set as a reference point which is a control group, and a positive control group was prepared by adding aminoguanidine of 1 μM, acarbose of 1 μM, glimepiride of 1 mM. A degree of insulin expression by treatment with 25 mM glucose as a negative control group was confirmed, and comparison and analysis whether or not the *Quamoclit angulata*-derived novel compound promoted insulin expression were conducted. The culture fluid of Min 6 cell cultured by the above-described method was obtained and an amount of the secreted insulin was measured using Insulin ELISA kit (R&D, UK).

Figure 6:
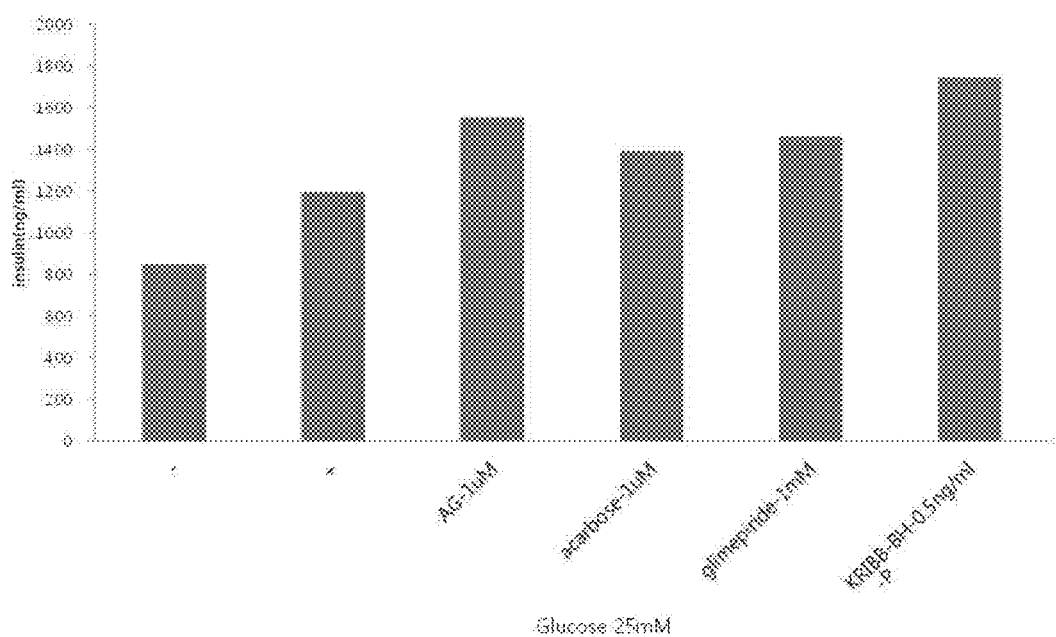
FIG. 6 is a graph showing the stimulation of insulin protein production in mouse pancreatic beta-cells by a novel compound isolated from *Quamoclit angulata*.

As a result, it was confirmed from FIG. 6 that insulin expression was increased in the pancreatic β cell line in which the novel compound KRIBB-BH-P was treated.

Example 5

Lens Culturing Experiment in Mouse

In the case of diabetic, a cataract is developed at an early stage, becomes rapidly worse and eyesight is rapidly deteriorated. Diabetes promotes opaque crystalline lens. Accordingly, diabetic cataract inhibition efficiency was examined by a lens culture experiment.

Eyes of a mouse was extracted and put into an iodine solution to be disinfected and then only the lens was extracted. The extracted eyes were put into M199 medium and cultured in a cell incubator. 20 mM xylose was added to the medium to induce lens opacity and the induced lens opacity was measured using CCD camera.

Figure 7:
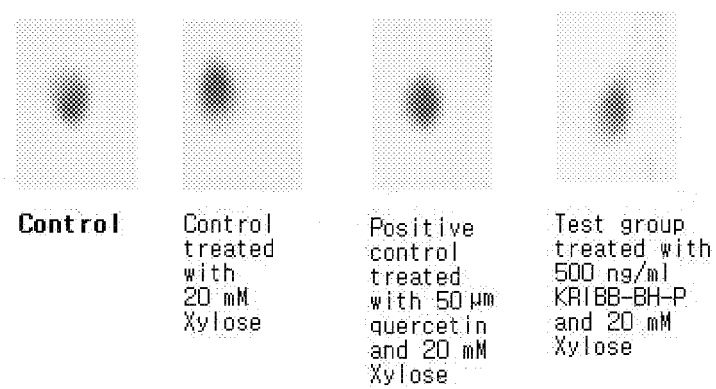
FIG. 7 shows the effect of a novel compound isolated from *Quamoclit angulata* on the reduction in the opacity of mouse lenses.

As a result, it was confirmed from FIG. 7 that the lens opacity was more inhibited in a group treated with the novel compound KRIBB-BH-P according to the present invention as compared to a positive control group treated with quercetin known as a material inhibiting cataract development.

Example 6

Diabetes Index Analysis of Diabetic Mouse Treated by *Quamoclit angulata*-Derived Novel Compound 6-1: Blood Glucose Analysis Normal mice and diabetic mice were treated with the *Quamoclit angulata*-derived novel compound and change in diabetic indexes including blood glucose, glycated hemoglobin, and urinary protein was confirmed.

6-week-old mice (Male C57BL/6J mouse, 20 g, Central Lab. Animal Inc., Seoul) and 6-week-old diabetic mice (Male C57BL/Ks DB/DB mouse, 20 g, Central Lab. Animal Inc., Seoul) were purchased and adopted under predetermined temperature (25° C.) and humidity (50%) for 1 week and used in an experiment.

A normal mouse control group, a diabetic mouse control group, a diabetic mouse group treated with drugs (glimepiride and acarbose), and a diabetic mouse group treated with *Quamoclit angulata*-derived novel compound were prepared, wherein each group had five mice, and each group treated with the combination administration of the *Quamoclit angulata*-derived novel compound was treated by oral administration at each concentration of 0.1 mg/kg, 1 mg/kg and 10 mg/kg and raised for 12 weeks. A change in blood glucose in mice of each group was measured every 2 weeks and urine was collected every 6 weeks to measure a urinary protein concentration, and mice was raised for 12 weeks and blood thereof was collected to measure glycated hemoglobin concentration.

Figure 8:
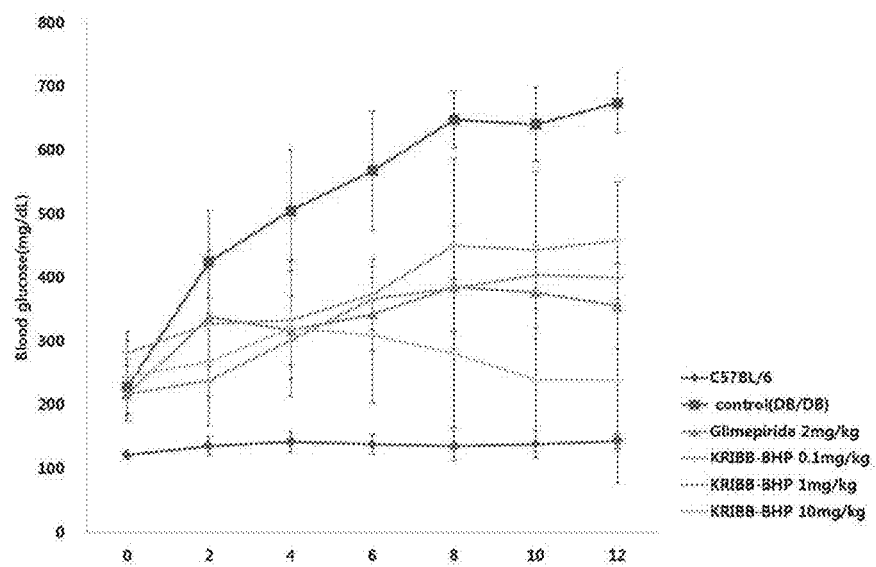
FIG. 8 shows the effect of a novel compound isolated from *Quamoclit angulata* on the lowering of blood glucose levels in diabetic model animals.

As a result, in a change in blood glucose, as shown in FIG. 8, blood glucose was increased in the diabetic mouse control group as compared to the normal mouse control group; however, in the diabetic mouse group treated with combination administration of the drugs and each group treated with *Quamoclit angulata*-derived novel compound by oral administration at each concentration of 0.1 mg/kg, 1 mg/kg and 10 mg/kg, blood glucose was remarkably decreased.

6-2: Glucose Tolerance Test

In order to conduct an oral glucose tolerance test, a 5-week-old mouse (Male C57BL/6J, 19 g, Koatech, Pyeongtaek-si, Gyeonggi-do, Korea) was purchased and adopted under predetermined temperature (25° C.) and humidity (50%) for 1 week and used in an experiment. A general diet group having a general feed as a food and a high-fat diet group having a high-fat feed as a feed were prepared, wherein each group had five mice, and raised for 2 weeks. At the time of two weeks after feeding with high-fat diet, the experimental mice were fasting for 16 hours, and the fasting blood glucose was measured, and then, the sample was orally administered at 1, 2, 4, 8, 16, and 24 hours before measuring the blood glucose, followed by oral administration of glucose 2 g/kg (body weight) and blood glucose thereof was measured every 30 minutes.

Figure 9:
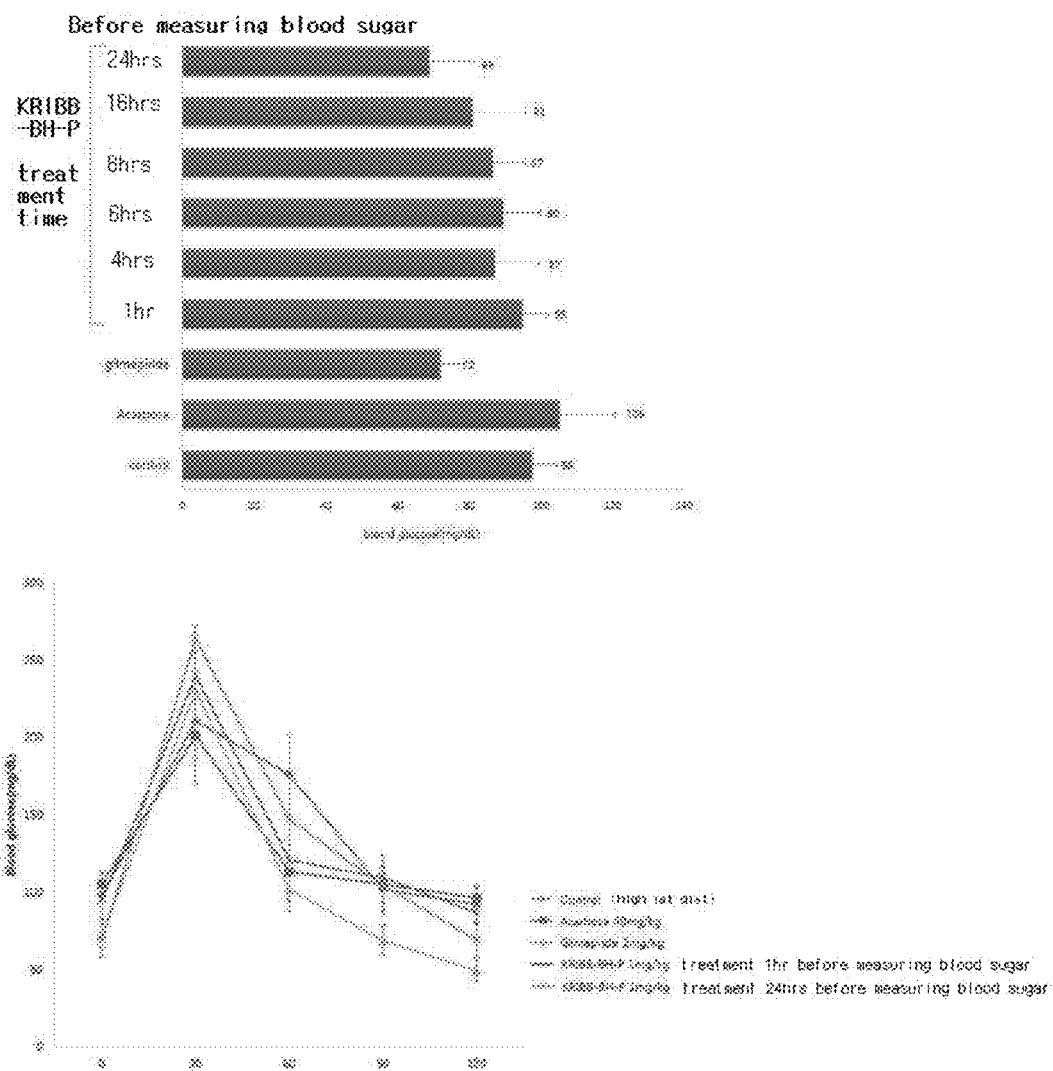
FIG. 9 shows the effect of a novel compound isolated from *Quamoclit angulata* on the reduction of blood sugar by glucose tolerance test.

As a result, as shown in FIG. 9, the group at the time of 24 hours after the sample was orally administered showed the highest efficacy.

6-3: Glycated Hemoglobin (HbAlc) Analysis

In order to decrease complications developed in patients receiving diabetes treatment, it is important to maintain blood glucose at an appropriate level. Since blood glucose measured at one time point may be changed by various factors, the most widely used test with a purpose of identifying a long-term change in regulation of blood glucose is glycated hemoglobin (HbAlc). A value of glycated hemoglobin in which sugar is combined with hemoglobin normally present in red blood cells is also increased when blood glucose is maintained at a high level. Since the glycated hemoglobin reflects an average blood glucose value for 2 to 4 months, it is useful for identify a degree of regulation of blood glucose in a long term.

In order to confirm effects of the *Quamoclit angulata*-derived novel compound on the glycated hemoglobin, blood of the normal mouse control group, the diabetic mouse control group and each diabetic mouse group treated with *Quamoclit angulata*-derived novel compound by oral administration at each concentration of 0.1 mg/kg, 1 mg/kg and 10 mg/kg were collected every 6 weeks and glycated hemoglobin was measured using enzyme-linked immunosorbent assay (ELISA) kit (Cusabio biotech, Japan).

Figure 10:
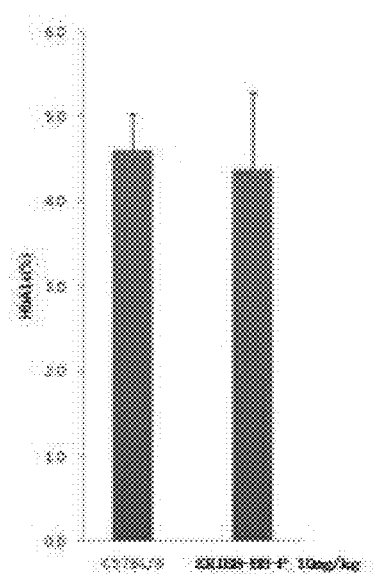
FIG. 10 shows the effect of a novel compound isolated from *Quamoclit angulata* on the inhibition of glycated hemoglobin in diabetic model animals.

As a result, as shown in FIG. 10, the glycated hemoglobin value was remarkably decreased in the diabetic mouse group treated with *Quamoclit angulata*-derived novel compound by oral administration at a concentration of 10 mg/kg as compared to the normal mouse control group.

6-4: Measurement of Creatinine

Diabetic patients are common to have both of kidney and heart complication. Diabetes may damage kidney which filters and excretes our body's waste. Through creatinine test, a concentration of creatinine in a blood may be measured and a function of kidney may be evaluated creatinine, which is a product obtained by dehydrating creatine produced after protein is used in muscle, is present in a blood with an extremely small amount. In the case in which a function of the kidney is deteriorated, creatinine may not be excreted. Urine and blood from diabetic model mouse of each group treated by oral administration for 12 weeks were collected, and creatinine was measured using ELISA kit (R&D, USA).

Figure 11:
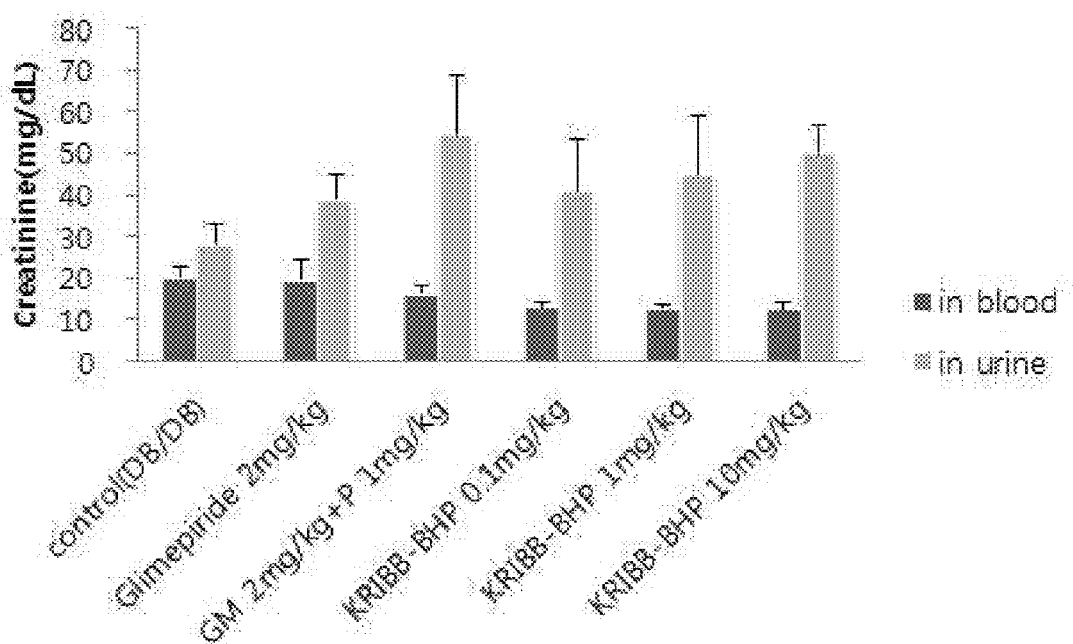
FIG. 11 shows the effect of a novel compound isolated from *Quamoclit angulata* on the normal excretion of creatine urine in diabetic model animals.

As a result, as shown in FIG. 11, it was confirmed that each concentration of creatinine in the bloods collected from the group treated with combination administration and the group treated with *Quamoclit angulata*-derived novel compound was decreased; however, each concentration of creatinine in the urines was increased, which showed that creatinine was readily excreted.

Example 7

Liver Toxicity and Liver Function Tests on Diabetic Mouse Treated with *Quamoclit angulata*-Derived Novel Compound 7-1: Concentration Analysis of Alanine Transaminase (ALT)

A 6-week-old mouse and a 6-week-old diabetic mouse which are the same as Example 5 above were adapted under predetermined temperature (25° C.) and humidity (50%) for 1 week and used in a liver toxicity test.

A normal mouse control group, a diabetic mouse control group, and each diabetic mouse group treated with *Quamoclit angulata*-derived novel compound by oral administration at each concentration of 0.1 mg/kg, 1 mg/kg and 10 mg/kg were prepared, wherein each group had five mice, and raised for 12 week. After raising the mice for 12 weeks, blood thereof was collected and a concentration of alanine transaminase was measured.

The alanine transaminase, which is a metabolic enzyme of amino acid, is used in a representative test for diagnosis and result observation. Maintenance in concentration of alanine transaminase indicates that there is no liver damage.

In order to confirm effects of the *Quamoclit angulata*-derived novel compound on liver, a normal mouse control group, a diabetic mouse control group and each group treated with *Quamoclit angulata*-derived novel compound by oral administration at each concentration of 0.1 mg/kg, 1 mg/kg and 10 mg/kg were raised for 12 weeks and blood thereof were collected and a change in alanine transaminase measured using ELISA kit (Cusabio biotech, Japan).

Figure 12:
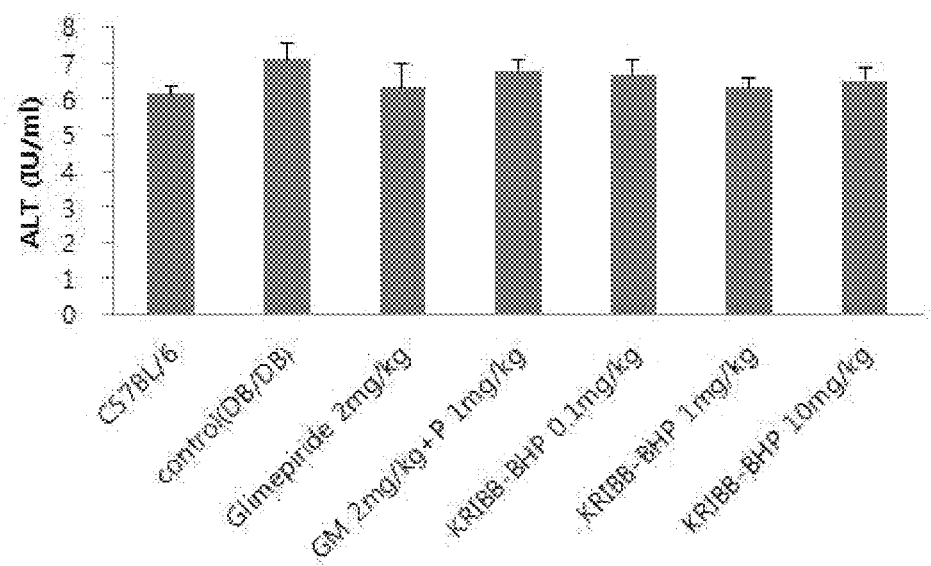
FIG. 12 shows the effect of a novel compound isolated from *Quamoclit angulata* on hepatotoxicity in diabetic model animals. There is no hepatotoxicity in diabetic model animals.

As a result, as shown in FIG. 12, it was confirmed that each diabetic mouse group treated with *Quamoclit angulata*-derived novel compound by oral administration at each concentration of 0.1 mg/kg, 1 mg/kg and 10 mg/kg had liver toxicity values which were similar to those of the normal mouse control group, and there was no liver toxicity in the groups treated with *Quamoclit angulata*-derived novel compound.

7-2: Bilirubin Analysis

Figure 13:
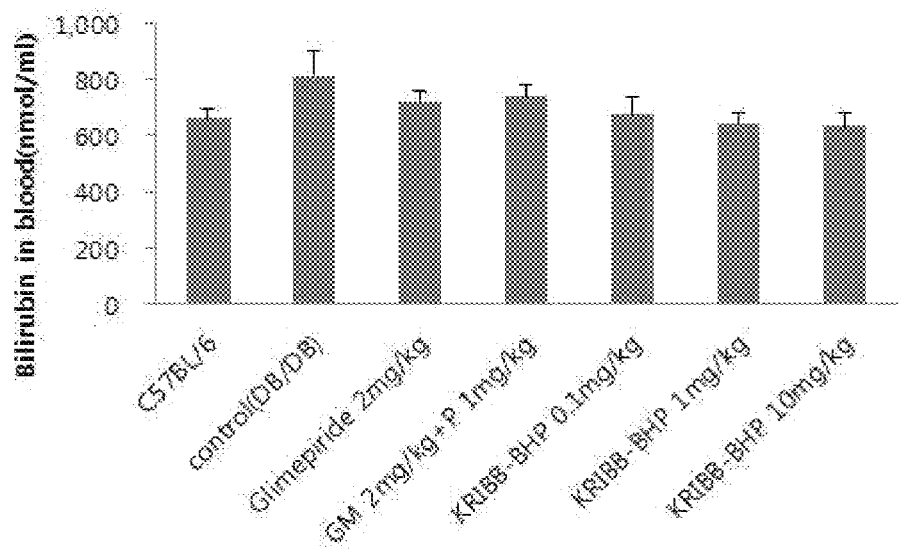
FIG. 13 shows the effect of a novel compound isolated from *Quamoclit angulata* on liver function in diabetic model animals. There is no disorder of liver function in diabetic model animals.

In order to confirm whether or not liver function was normal in the group treated with *Quamoclit angulata*-derived novel compound, bilirubin value was measured using ELISA kit (Cusabio biotech, Japan) using blood collected in Example above. As a result of Bilirubin analysis, as shown in FIG. 13, bilirubin value of the group treated with *Quamoclit angulata*-derived novel compound was included in a normal range. Therefore, it may be appreciated that the composition of the present invention is safe composition not causing abnormal liver function.

Example 8

Analysis of Insulin Resistance and β-cell Functionality of Diabetic Mouse Treated with *Quamoclit angulata*-Derived Novel Compound Insulin and blood glucose of the diabetic mouse group raised under conditions of Example 7 above were measured by the fasting blood test or glucose tolerance test and insulin sensitivity index thereof was calculated.

Insulin resistance was evaluated using the insulin sensitivity index which is homeostasis assessment (HOMA)-IR and β-cell Functionality was evaluated by HOMA-beta.

Figure 14:
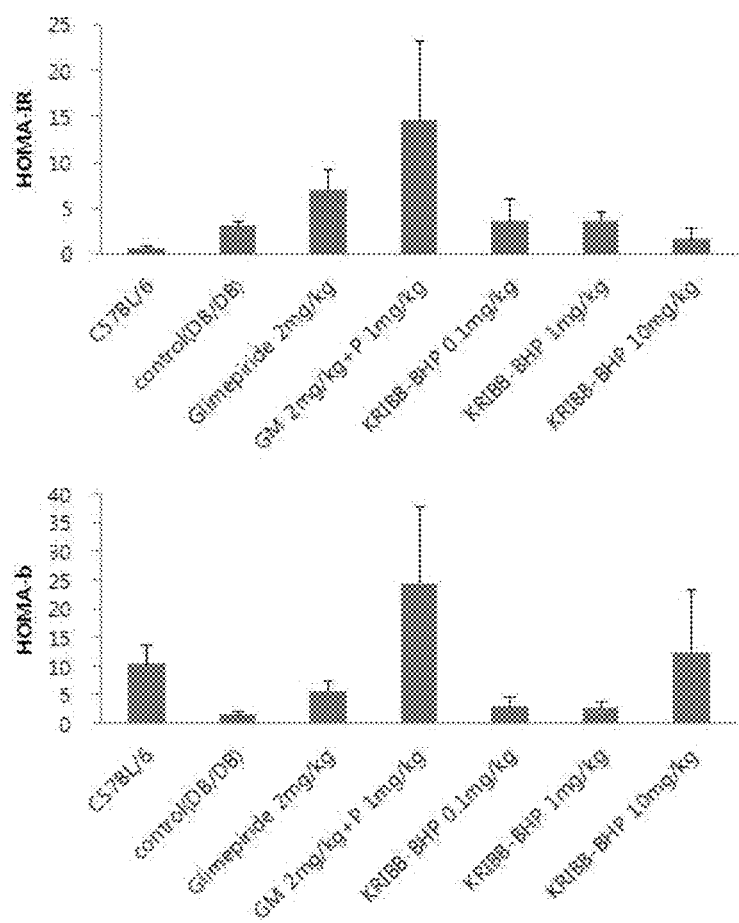
FIG. 14 shows the effect of a novel compound isolated from *Quamoclit angulata* on the improvement of beta-function and the reduction of insulin glucose tolerance in diabetic model animals.

As a result, as shown in FIG. 14, the group treated with *Quamoclit angulata*-derived novel compound showed remarkably excellent result.

HOMA-IR=(Fasting insulin (μIU/mL)×Fasting glucose (nmol/L))/22.5

HOMA-beta=20×Fasting insulin (U/mL)/Fasting glucose (mmol/L)−3.5

Example 9

**Adiponectin Concentration Analysis in Blood of Diabetic Mouse Treated with *Quamoclit angulata*-Derived Novel Compound**

It has consistently proven that adiponectin is secreted from fat cells and abundantly present in blood, is decreased in an obesity patient or type 2 diabetic. In addition, low hypoadiponectinemia is on the rise as a new risk factor of artherosclerotic disease, and a concentration of adiponectin in diabetic patients, in particular, patients accompanying macrovascular complications is decreased. That is, adiponectin has an anti-obesity action, an anti-diabetic action, anti-atherogenic action and an inhibition action of active oxygen generation. A concentration of adiponectin in the blood of the diabetic mouse group raised under conditions of Example 7 was measured using ELISA kit (R&D, USA).

Figure 15:
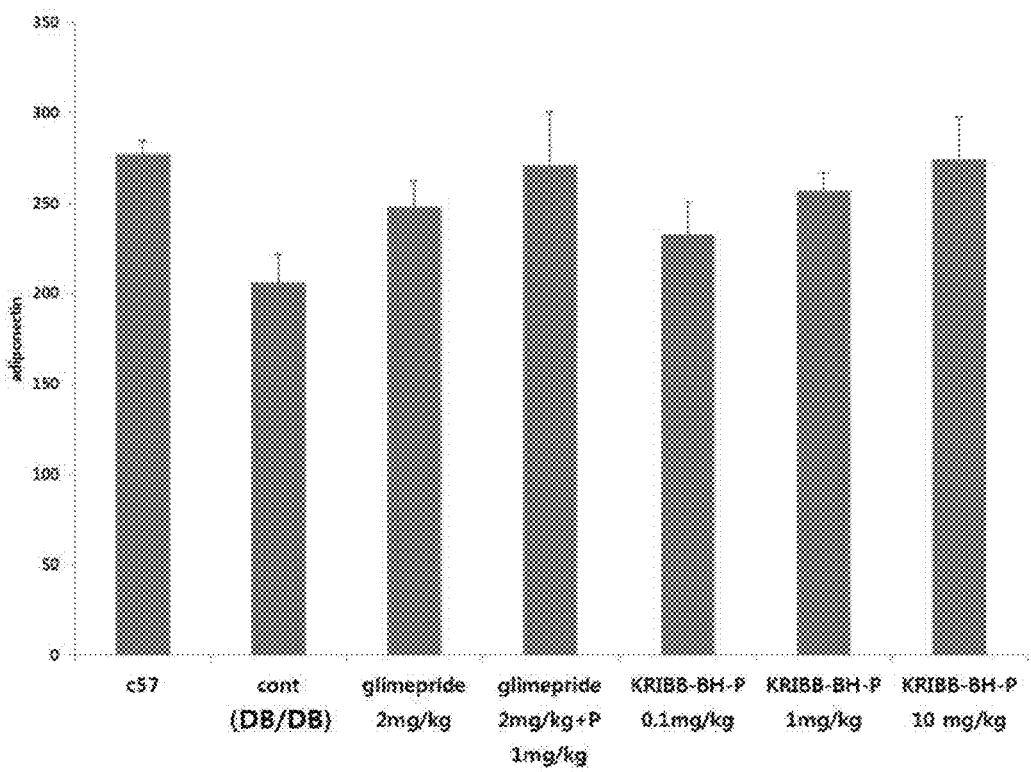
FIG. 15 shows the effect of a novel compound isolated from *Quamoclit angulata* on increasing the expression of adiponectin in diabetic model animals.

As a result, as shown in FIG. 15, it was confirmed that expression of adiponectin, which is a value showing an improvement of insulin resistance, was decreased in the diabetic mouse control group; however, in the other groups, in particular, the experimental group treated with *Quamoclit angulata*-derived novel compound, expression of adiponectin was increased.

Example 10

**Glucagon Concentration Analysis of Diabetic Mouse Treated with *Quamoclit angulata*-Derived Novel Compound**

As hormones playing a key role in maintaining an appropriate blood glucose value, there are glucagon increasing glucose as well as insulin removing glucose.

In type 2 diabetic patients, blood glucose is increased, insulin secretion by glucose intake is delayed, and glucagon is increased. It is generally known that decrease in a ratio of insulin to plasma glucagon is associated with deterioration of diabetes. Therefore, a concentration of glucagon of the diabetic mouse group raised under conditions of Example 7 above was confirmed.

Figure 16:
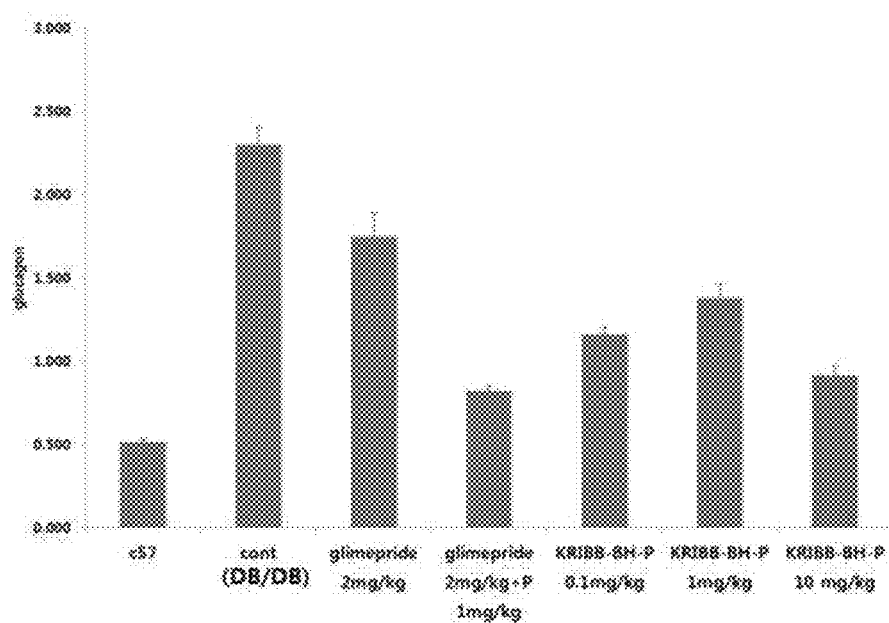
FIG. 16 shows the effect of a novel compound isolated from *Quamoclit angulata* on decreasing the expression of glucagon in diabetic model animals.

As a result, as shown in FIG. 16, a concentration of plasma glucagon in the diabetic control group was remarkably high as compared to the normal control group; however, the concentration of plasma glucagon in the diabetic control group treated with the novel compound according to the present invention was remarkably decreased to be lower than that of the group treated with the drugs. A ratio of insulin to glucagon in the diabetic control group was remarkably low as compared to the normal group. Therefore, due to administration of *Quamoclit angulata*-derived novel compound, the concentration ratio of insulin to glucagon in the group treated with *Quamoclit angulata*-derived novel compound was remarkably increased as compared to the diabetic mouse control group, and thus, it could be appreciated that the *Quamoclit angulata*-derived novel compound may normalize abnormal concentration of insulin and glucagon caused by diabetes and inhibit deterioration of diabetes.

Example 11

**Dipeptidyl peptidase IV (DPP-IV) Inhibition Efficacy Analysis of Diabetic Mouse Treated with *Quamoclit angulata*-Derived Novel Compound**

There are two kinds of incretin such as glucose dependent insulinotropic eptide (GIP) and glucagon like peptide (GLP-1), and when glucose is increased in small intestine, two hormones are both secreted from endocrine cell in an epithelial cell layer of small intestine to thereby stimulate β-cell of the pancreas, promote insulin secretion, and inhibit glucagon secretion in α-cell.

Therefore, incretin drops blood glucose dependent on concentration of orally ingested glucose and low blood glucose is hardly induced. Both of GIP and GLP-1 are rapidly decomposed by dipeptidyl peptidase (DPP)-4 which is a series of serine protease. DPP-4 inhibition efficacy of the diabetic mouse group raised under conditions of Example 7 above was confirmed based on the above description.

Figure 17:
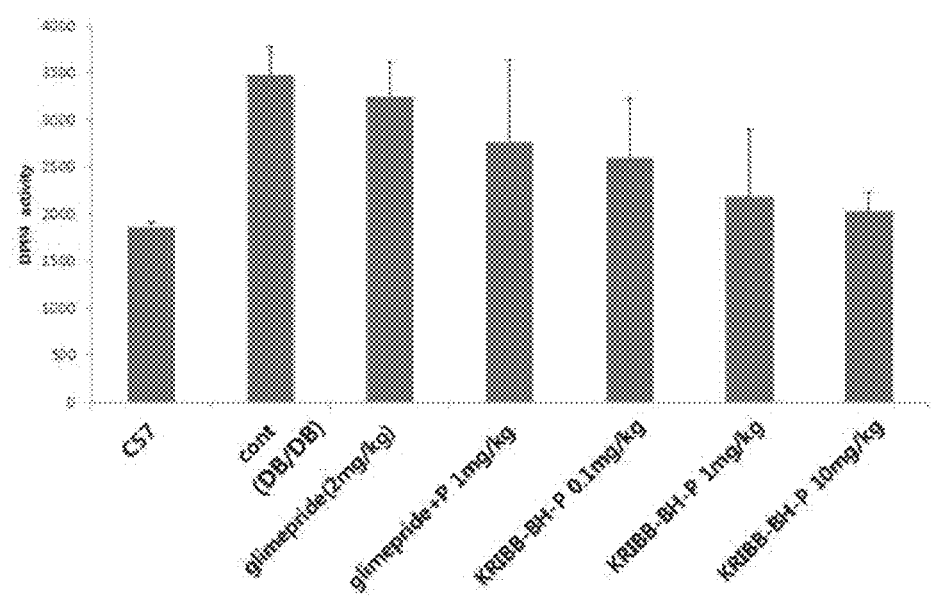
FIG. 17 shows the effect of a novel compound isolated from *Quamoclit angulata* on the inhibition of DPP-IV activity in diabetic model animals.

As a result, as shown in FIG. 17, it could be appreciated that an activity of DPP IV was inhibited in the group treated with the *Quamoclit angulata*-derived novel compound. Through inhibition in the activity of DPP-IV spotlighted as a target of novel treatment against diabetes, an increase in glycated hemoglobin and blood glucose may be inhibited and excellent effect for prevention or treatment of diabetes may be provided.

Example 12

**Alpha-Glucosidase Activity Inhibition Ratio Measurement of Diabetic Mouse Treated with *Quamoclit angulata*-Derived Novel Compound**

Alpha-glucosidase inhibitor inhibits a function of alpha-glucosidase distributed in intestinal mucosa to thereby inhibit postcibal blood glucose from being increased. That is, alpha-glucosidase has a role of decomposing polysaccharide into monosaccharide to promote absorption of monosaccharide into small intestine, wherein the novel compound inhibits such role and hinders absorption of monosaccharide to thereby delay digestion and absorption of carbohydrate in the ingested feed to decrease a rise in postcibal blood glucose and insulin in blood, thereby showing treatment effect of diabetes. The alpha-glucosidase inhibitor does not induce hyperinsulinemia or hypoglycemia but promotes secretion of glucagon-like peptide-1 promoting insulin secretion and inhibiting glucagon secretion at a small intestine.

Activity of alpha-glucosidase of the diabetic mouse group raised under conditions of Example 7 above was measured based on the above-description.

Figure 18:
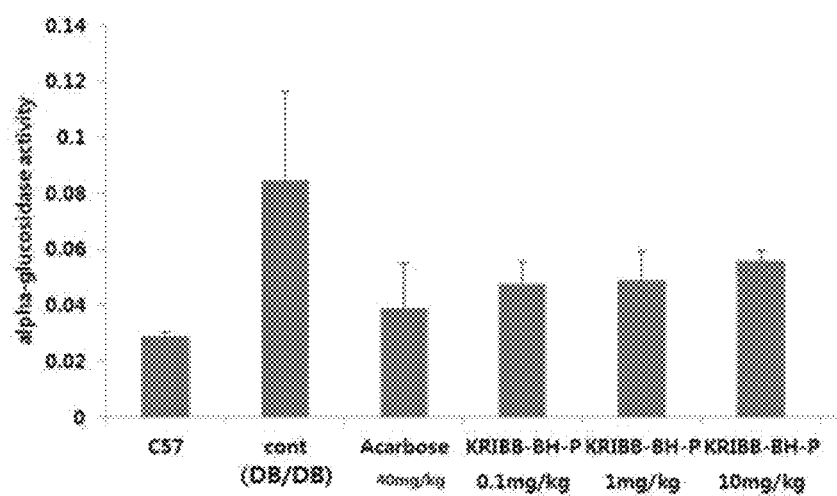
FIG. 18 shows the effect of a novel compound isolated from *Quamoclit angulata* on the inhibition of α-glucosidase activity in diabetic model animals.

As a result, as shown in FIG. 18, it could be appreciated that activity of alpha-glucosidase of the group treated with the novel compound of the present invention was inhibited.

Example 13

**Tumor Necrosis Factor-Alpha (TNF-Alpha) of Diabetic Mouse Treated with *Quamoclit angulata*-Derived Novel Compound**

Tumor necrosis factor-alpha (TNF-α) is mainly expressed in a fat cell, an increase level of the cytokine is associated with obesity and insulin resistance. A fat tissue produces cytokines such as tumor necrosis factor-alpha (TNF-α), resistin, interleukin-6(IL-6), wherein it was confirmed that the cytokines inhibit insulin action. In an obese person, sympathetic nerve activity is increased, which increases fat decomposition and decreases blood flow of muscle (glucose transport) to thereby directly affect insulin action. Tumor necrosis factor-alpha (TNF-α) increases blood glucose to induce diabetes and enters into blood vessel to prevent inflammation and to prevent secretion of adiponectin inhibiting built-up cholesterol, thereby hindering NF-kB signal transfer into vascular endothelial cell and inhibiting activity of phagocytosis by macrophage.

TNF-α concentration of the diabetic mouse group raised under conditions of Example 7 above was measured based on the above-description.

Figure 19:
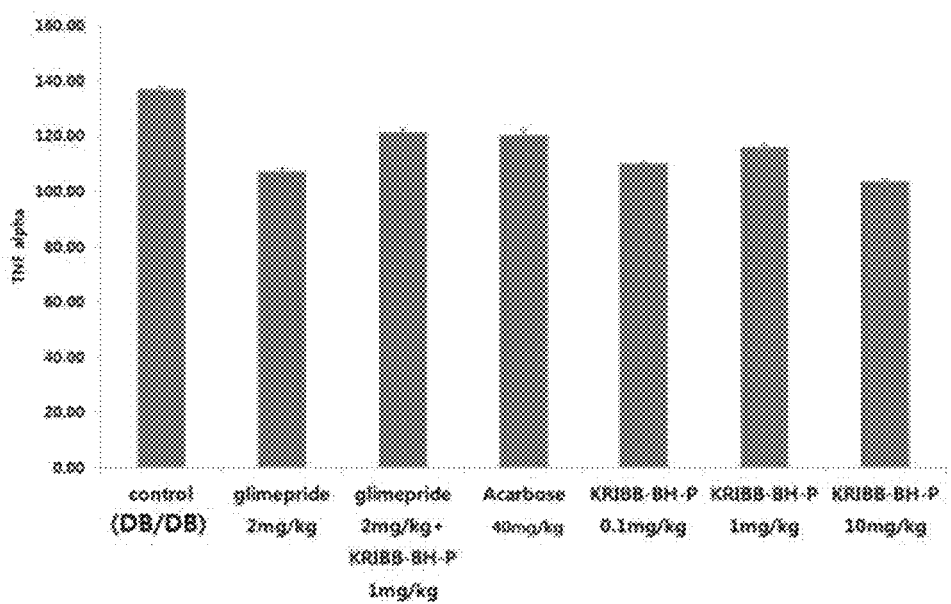
FIG. 19 shows the effect of a novel compound isolated from *Quamoclit angulata* on decreasing the expression of tumor necrosis factor alpha in diabetic model animals.

As a result, as shown in FIG. 19, it could be appreciated that TNF-α concentration of the diabetic mouse group treated with quamoclit *angulata*-derived novel compound was decreased.

Example 14

Anti-Cataract Effect of Diabetic Mouse Treated with *Quamoclit angulata*-Derived Novel Compound Eye lens was isolated from eyeball extracted from the diabetic mouse group raised under conditions of Example 7 above and moved to a well plate and then a photograph thereof was taken by LAS 3000 image analysis system. Turbidity of the eye lens was measured by analyzing the photograph using LAS 300 image analysis program.

Figure 20:
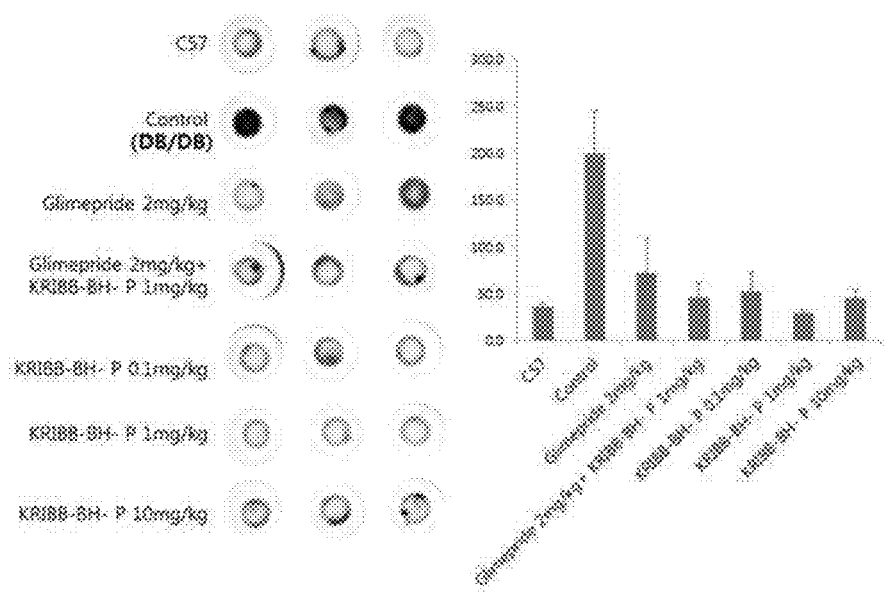
FIG. 20 shows the effect of a novel compound isolated from *Quamoclit angulata* on anti-cataract in diabetic model animals.

As a result, as shown in FIG. 20, it could be appreciated that turbidity in the group treated with *Quamoclit angulata*-derived novel compound was decreased. Although specific embodiments of the present invention are described in detail, it will be apparent to those skilled in the art that the specific description is merely desirable exemplary embodiment and should not be construed as limiting the scope of the present invention. Therefore, the substantial scope of the present invention will be defined by the accompanying claims and their equivalents.

INDUSTRIAL APPLICABILITY

As described above, the novel compound isolated from *Quamoclit* sp. according to the present invention has excellent effects on lowering blood sugar, promoting insulin secretion, inhibiting VEGF expression, and so on. Thus, the present invention not only functions to prevent or treat diabetes and its complications, but also functions to promote treatment effects when treated together with conventional diabetes medicines.

The invention claimed is:

1. A method for preparing a compound of chemical formula 2, the method comprising the steps of:
    (a) extracting *Quamoclit* sp. with a solvent selected from the group consisting of water, alcohol, an organic solvent, and mixtures thereof, thereby preparing *Quamoclit* extract;
    (b) suspending the *Quamoclit* extract by adding water thereto, and fractionating with normal hexane, ethyl acetate and butanol, thereby obtaining water fraction; and
    (c) isolating and purifying the water fraction, thereby obtaining the compound of chemical formula 2:

(chemical formula 2)

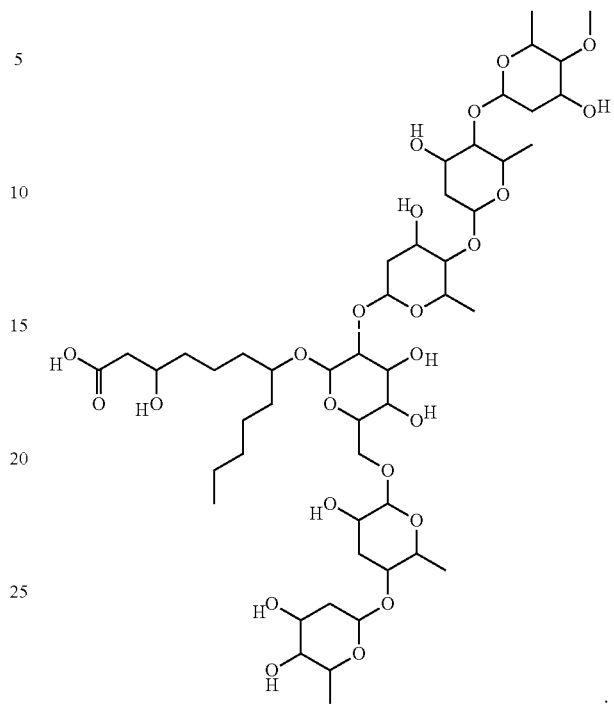

2. The method of claim 1, wherein the *Quamoclit* sp. is *Quamoclit* angulata.

3. A method of treating diabetes and its complications, by administering to a subject in need thereof a pharmaceutical composition, which contains a compound of chemical formula 1 or salt thereof as an active ingredient:

(chemical formula 1)

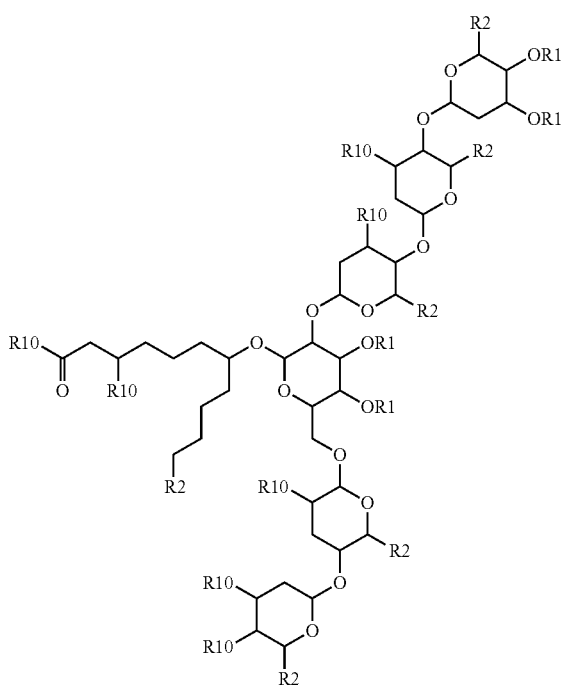

wherein R1 and R2 are independently hydrogen or C$_{1-20}$ alkyl group.

4. The method of claim 3, wherein the pharmaceutical composition comprises a structure of chemical formula 2:

(chemical formula 2)

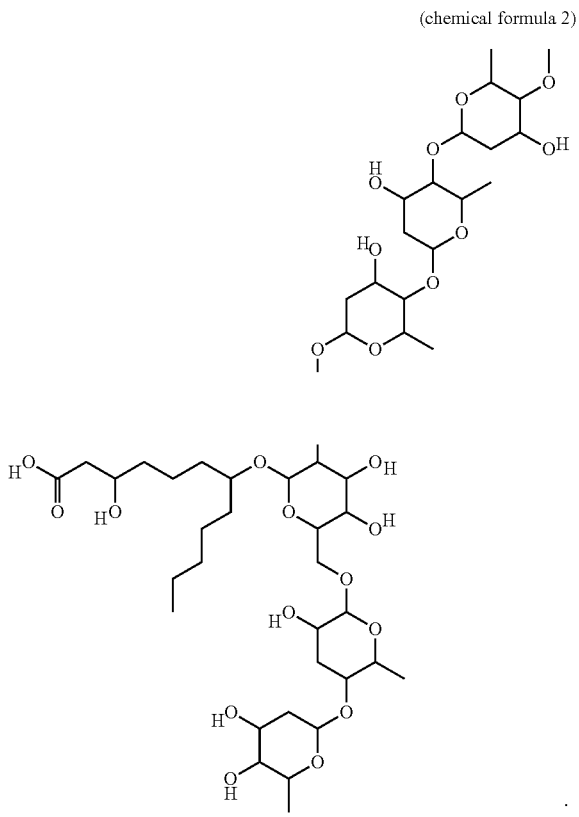

5. The method of claim 3, wherein the complications are selected from the group consisting of hyperglycemia, hyperinsulinemia, insulin resistance, dyslipidemia, impaired fasting glucose, impaired glucose tolerance, obesity, arteriosclerosis, microangiopathy, renal disease, heart disease, foot ulcer, arthritis, osteoporosis, and ophthalmologic disease induced by diabetes.

6. The method of claim 5, wherein the ophthalmologic disease induced by diabetes is selected from the group consisting of diabetic retinopathy, cataract, macular degeneration, external ophthalmoplegia, iridocyclitis, optic neuritis, glaucoma, retinal degeneration, fundus hemorrhage, anomalies of refraction, subconjunctival hemorrhage, and vitreous hemorrhage.

7. The method of claim 3, wherein the pharmaceutical composition further comprises an antidiabetic compound.

8. The method of claim 7, wherein the antidiabetic compound is selected from the group consisting of nateglinide, repaglinide, glitazones, sulfonylureas, metform in, glimepiride, thiazolidinediones, biguanides, acarbose which is α-glucosidase inhibitor, and prandin of meglitinides.

9. A method of relieving diabetes and its complications, by administering to a subject in need thereof a health functional food, which contains a compound of chemical formula 1 or salt thereof as an active ingredient:

(chemical formula 1)

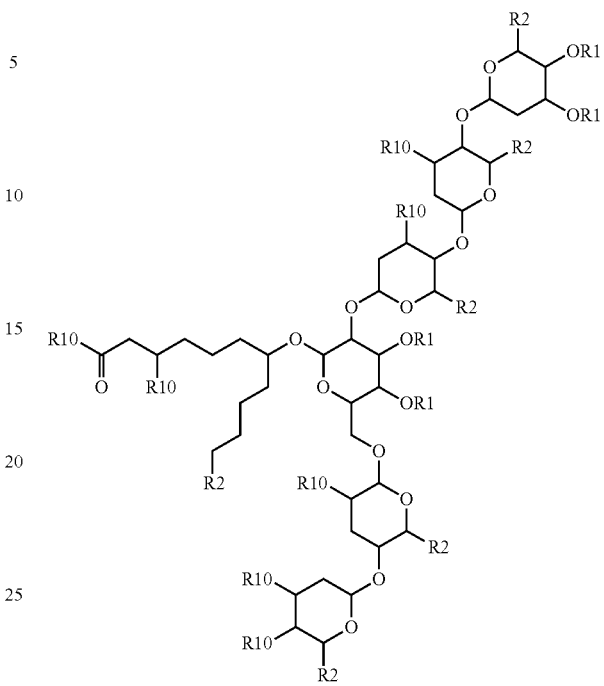

wherein R1 and R2 are independently hydrogen or C$_{1-20}$ alkyl group.

10. The method of claim 9, wherein the health functional food comprises a structure of chemical formula 2:

(chemical formula 2)

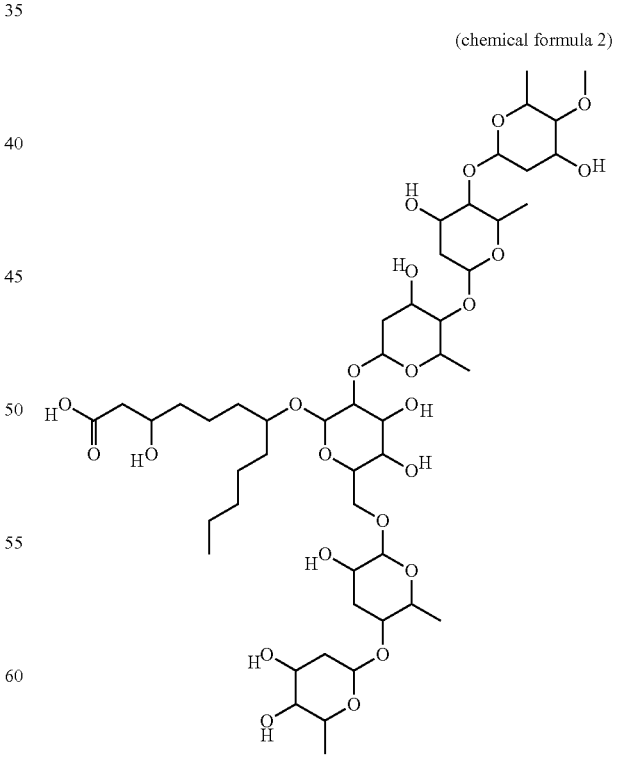

11. The method of claim 9, wherein the complications are selected from the group consisting of hyperglycemia, hyperinsulinemia, insulin resistance, dyslipidemia, impaired fasting glucose, impaired glucose tolerance, obesity, arteriosclerosis, microangiopathy, renal disease, heart disease, foot ulcer, arthritis, osteoporosis, and ophthalmologic disease induced by diabetes.

12. The method of claim 11, wherein the ophthalmologic disease induced by diabetes is selected from the group consisting of diabetic retinopathy, cataract, macular degeneration, external ophthalmoplegia, iridocyclitis, optic neuritis, glaucoma, retinal degeneration, fundus hemorrhage, anomalies of refraction, subconjunctival hemorrhage, and vitreous hemorrhage.

* * * * *